(12) United States Patent
Moyer et al.

(10) Patent No.: US 10,765,791 B2
(45) Date of Patent: Sep. 8, 2020

(54) DETERMINATION OF CARDIAC PARAMETERS FOR MODULATION OF BLOOD PUMP SUPPORT

(71) Applicant: Abiomed, Inc., Danvers, MA (US)

(72) Inventors: Christian Moyer, Danvers, MA (US);
Scott C. Corbett, Danvers, MA (US);
Ahmad El Katerji, Danvers, MA (US);
David Weber, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 103 days.

(21) Appl. No.: 16/003,669

(22) Filed: Jun. 8, 2018

(65) Prior Publication Data
US 2018/0353667 A1 Dec. 13, 2018

Related U.S. Application Data

(60) Provisional application No. 62/517,668, filed on Jun. 9, 2017, provisional application No. 62/635,662, filed on Feb. 27, 2018.

(51) Int. Cl.
*A61M 1/10* (2006.01)
*A61B 5/0215* (2006.01)
*A61B 5/029* (2006.01)

(52) U.S. Cl.
CPC .......... *A61M 1/1086* (2013.01); *A61B 5/029* (2013.01); *A61B 5/0215* (2013.01);
(Continued)

(58) Field of Classification Search
CPC .............. A61M 1/1008; A61M 1/1086; A61M 2205/18; A61M 2205/3334;
(Continued)

(56) References Cited

U.S. PATENT DOCUMENTS 3,677,092 A 7/1972 Guarino
3,911,897 A 10/1975 Leachman, Jr.
(Continued)

FOREIGN PATENT DOCUMENTS

EP 2 298 375 A1 3/2011
WO WO-97/49439 A1 12/1997
(Continued)

OTHER PUBLICATIONS

PCT International Search Report for PCT/US2018/036757, dated Sep. 10, 2018 (5 pages).
(Continued)

*Primary Examiner* — George Manuel
(74) *Attorney, Agent, or Firm* — Botos Churchill IP Law LLP

(57) ABSTRACT

The systems, devices, and methods presented herein use a blood pump to obtain measurements of cardiac function. The system can quantify the functioning of the native heart by measuring certain parameters/signals such as aortic pressure or motor current, then calculate and display one or more cardiac parameters and heart function parameters, such as left ventricular pressure, left ventricular end diastolic pressure, or cardiac power output. These parameters provide valuable information to a user regarding current cardiac function, as well as positioning and function of the blood pump. In some embodiments, the system can act as a diagnostic and therapeutic tool. Providing cardiac parameters in real-time, along with warnings about adverse effects and recommendations to support cardiac function, such as increasing or decreasing the volumetric flow rate of blood pumped by the device, administering pharmaceutical therapies, and/or repositioning the blood pump allow clinicians to better support and treat cardiovascular disease.

20 Claims, 16 Drawing Sheets

(52) U.S. Cl.
CPC ....... *A61M 1/1008* (2014.02); *A61M 2205/18* (2013.01); *A61M 2205/3334* (2013.01); *A61M 2205/3344* (2013.01); *A61M 2205/3365* (2013.01); *A61M 2205/502* (2013.01); *A61M 2205/52* (2013.01); *A61M 2210/125* (2013.01); *A61M 2210/127* (2013.01); *A61M 2230/30* (2013.01)

(58) Field of Classification Search
CPC .. A61M 2205/3344; A61M 2205/3365; A61M 2205/502; A61M 2205/52; A61M 2210/125; A61M 2210/127; A61M 2230/30; A61B 5/0215; A61B 5/029
See application file for complete search history.

(56) References Cited

U.S. PATENT DOCUMENTS

| | | | |
|---|---|---|---|
| 4,598,579 | A | 7/1986 | Cummings et al. |
| 5,437,284 | A | 8/1995 | Trimble |
| 6,159,160 | A | 12/2000 | Hsei et al. |
| 6,176,822 | B1 | 1/2001 | Nix et al. |
| 6,234,759 | B1 | 5/2001 | Hennel et al. |
| 6,623,420 | B2 | 9/2003 | Reich et al. |
| 7,010,954 | B2 | 3/2006 | Siess et al. |
| 7,022,100 | B1 | 4/2006 | Aboul-Hosn et al. |
| 7,192,403 | B2 * | 3/2007 | Russell ............ A61B 5/02007 600/485 |
| 2003/0139643 | A1 | 7/2003 | Smith et al. |
| 2004/0039243 | A1 | 2/2004 | Beamson et al. |
| 2004/0106874 | A1 | 6/2004 | Eigler et al. |
| 2008/0097226 | A1 | 4/2008 | McConnell |
| 2010/0222635 | A1 | 9/2010 | Poirier |
| 2012/0095523 | A1 | 4/2012 | Yared |
| 2013/0046129 | A1 | 2/2013 | Medvedev et al. |
| 2014/0296615 | A1 | 10/2014 | Franano |
| 2015/0073203 | A1 | 3/2015 | Wariar et al. |
| 2015/0246166 | A1 | 9/2015 | Greatrex et al. |
| 2016/0367740 | A1 | 12/2016 | Aboul-Hosn et al. |
| 2017/0136164 | A1 | 5/2017 | Yeatts |
| 2017/0239407 | A1 | 8/2017 | Hayward |
| 2018/0146864 | A1 | 5/2018 | Jansen et al. |

FOREIGN PATENT DOCUMENTS

| | | |
|---|---|---|
| WO | WO-98/43688 A1 | 10/1998 |
| WO | WO-03/015609 A2 | 2/2003 |
| WO | WO-03/082379 A1 | 10/2003 |
| WO | 2004/017818 A2 | 3/2004 |
| WO | WO-2005/051838 A2 | 6/2005 |
| WO | WO-2010/099287 A1 | 9/2010 |
| WO | WO-2011/090927 A1 | 7/2011 |
| WO | WO-2014/062911 A2 | 4/2014 |
| WO | WO-2014/085806 A1 | 6/2014 |
| WO | WO-2015/040222 A2 | 3/2015 |
| WO | WO-2018/036927 A1 | 3/2018 |
| WO | WO-2018/073150 A1 | 4/2018 |
| WO | WO-2018/146045 A1 | 8/2018 |

OTHER PUBLICATIONS

International Search Report PCT/U52017/052259, dated Dec. 19, 2017 (4 pages).
International Search Report PCT/U52019/038039, dated Sep. 5, 2019 (6 pages).
International Search Report PCT/US2019/038049, dated Sep. 5, 2019 (6 pages).
International Search Report for PCT/EP2017/070953, dated Nov. 20, 2017 (3 pages).
International Search Report for PCT/EP2017/076295, dated Jan. 15, 2018 (6 pages).
International Search Report PCT/U52019/044032, dated Nov. 6, 2019 (2 pages).
Rüschen et al., "Online cardiac output estimation during transvalvular left ventricular assistance," Computer Methods and Programs in Biomedicine, vol. 171: 87-97 (2019).
Rüschen et al., "Robust Assistance Control of Left Ventricular Assist Devices," IFMBE Proceedings, vol. 65(13): 294-297 (2017).
Sekii et al., "Beat-to-Beat Prediction of Left Ventricular Output During Left Ventricular Bypass Pumping," Proceedings of the Annual International Conference of the IEEE Engineering in Medicine and Biology Society: 10th Annual International Conference—Nov. 4, 1988: 1773-1775.
Stolinski, et al, "The heart-pump interaction: Effects of a microaxial blood pump", International Journal of Artificial Organs, vol. 25, No. 11, pp. 1082-1088 (2002).

* cited by examiner

DETERMINATION OF CARDIAC PARAMETERS FOR MODULATION OF BLOOD PUMP SUPPORT

CROSS-REFERENCE TO RELATED APPLICATIONS

This application claims priority to U.S. Provisional Application 62/517,668, filed Jun. 9, 2017, titled "Determination of Cardiac Parameters for Modulation of Blood Pump Support," and to U.S. Provisional Application 62/635,662, filed Feb. 27, 2018, titled "Determination of Cardiac Parameters for Modulation of Blood Pump Support," the contents of each of which are incorporated in their entirety by reference herein.

BACKGROUND

Intravascular blood pumps provide hemodynamic support and facilitate heart recovery. Intravascular blood pumps are inserted into the heart and supplement cardiac output in parallel with the native heart to provide supplemental cardiac support to patients with cardiovascular disease. An example of such a device is the IMPELLA® family of devices (Abiomed, Inc., Danvers Mass.).

Currently, it is difficult for clinicians to directly and quantitatively determine the amount of support a device should deliver or when to terminate use of a cardiac assist device. Thus, clinicians tend to rely on qualitative judgments and indirect estimates of cardiac function, such as measuring intracardiac or intravascular pressures using fluid filled catheters. Traditionally, left-ventricular pressure (LVP) is estimated by measurement of a Pulmonary Arterial Wedge Pressure (PAWP) or Pulmonary Capillary Wedge Pressure (PCWP) in which a pulmonary catheter including a balloon is inserted into a pulmonary arterial branch. PAWP and PCWP are not an effective measurement of cardiac health, as the pulmonary arterial catheters are intermittent, indirect, and inconsistent, resulting in incorrect data which cannot be used reliably by clinicians to make clinical decisions regarding the level of cardiac support required by a patient.

Blood pumps provide supplemental cardiac support by assisting in pumping blood through the chambers of the heart, for example from the left ventricle or atrium into the aorta, and from the right atrium or ventricle into the pulmonary artery. Blood pumps are typically inserted to assist with cardiac support for a time period, after which the patient is weaned from the blood pump support, allowing the heart to pump blood unsupported. Because clinicians do not have access to reliable information about cardiac function, patients are often weaned too early and too quickly causing unnecessary strain on the heart.

Accurate measurements of left-ventricular pressure, cardiac power output and other cardiac variables could allow clinicians to make better clinical decisions for patients based on the current needs of the heart. Accordingly, there is a long-felt need for improvements over the present day systems providing information about cardiac support and cardiac health to clinicians.

SUMMARY

In some implementations, a method for providing cardiac support to a heart includes operating a blood pump positioned in the heart, the blood pump having a cannula, a motor operating at a motor speed and drawing a variable current to provide a level of cardiac support to the heart. The blood pump also includes a controller coupled to the blood pump. The method also includes the controller measuring an aortic pressure, measuring the motor current and the motor speed, determining a pressure gradient across the cannula associated with the motor current and the motor speed, using a processor to calculate a calculated cardiac parameter from the aortic pressure and the pressure gradient across the cannula associated with the motor current and the motor speed, for example the left-ventricular pressure (LVP) or left-ventricular end-diastolic pressure (LVEDP). The method also includes recording the calculated cardiac parameter in a memory and using the calculated cardiac parameter to determine a heart function parameter, for example a measure of cardiac power output. The method continues by determining a recommended change to the support provided by the blood pump based on the calculated cardiac parameter and the heart function parameter, and generating the recommended change to the support for display. The recommended change to the support may be, for example, a recommendation for increasing or decreasing the motor speed during weaning, a recommendation to adjust the positioning of the blood pump in response to a suction event, or a recommendation to change to a different blood pump having different capabilities, among other recommendations. The method may also include generating for display the calculated cardiac parameters and heart function parameters. Displaying important cardiac parameters and heart function parameters allow health care professionals to make informed decisions about the modulation of blood pump support to patients. Further, the calculation of these parameters based on the motor current and the motor speed of the blood pump and measured aortic pressure enable the determination of recommendations for modulation and adjustment of the blood pump that can be provided to health care professionals to aid in the determination of possible issues and to prompt adjustments in care.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
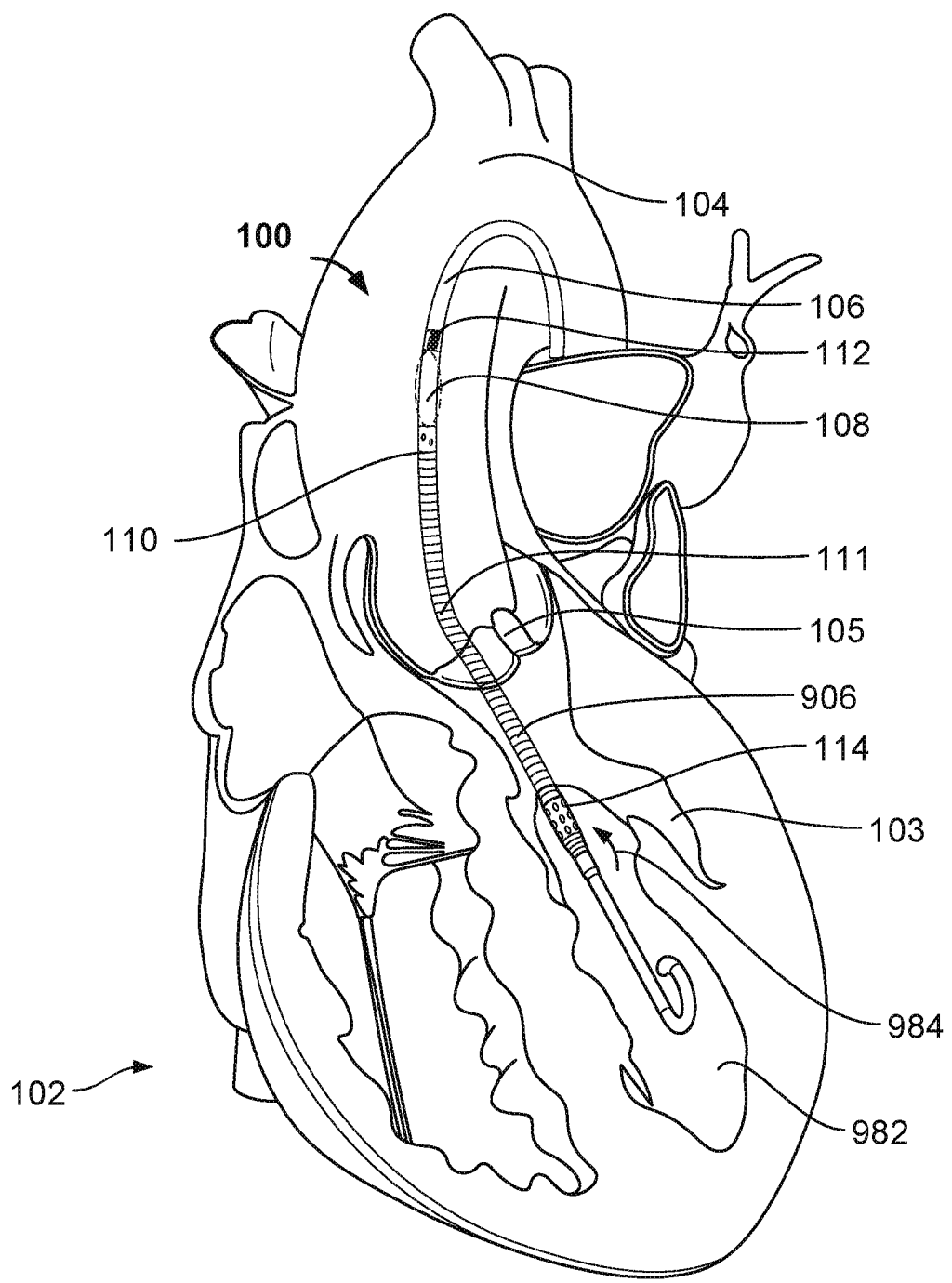
FIG. 1 shows an intravascular heart pump system located in a heart.

To provide an overall understanding of the systems, method, and devices describe herein, certain illustrative embodiments will be described. Although the embodiments and features described herein are specifically described for use in connection with a percutaneous blood pump system, it will be understood that all the components and other features outlined below may be combined with one another in any suitable manner and may be adapted and applied to other types of cardiac therapy and cardiac assist devices, including cardiac assist devices implanted using a surgical incision, and the like.

The systems, devices, and methods described herein provide mechanisms for providing cardiac parameters and heart function parameters to clinicians based on the motor current, the motor speed, and the aortic pressure measured at a blood pump system. The functionality and output of the intravascular blood pump, along with measurable cardiac parameters, can be used to calculate additional parameters useful in determining patient cardiac performance and health. By making these determinations and displaying the data to a clinician in a useful and meaningful way, the clinician has more data available to inform healthcare decisions. The additional cardiac parameters and heart functions, as well as trends in the same, accessible by algorithms based on the intravascular blood pump output, allow clinicians to make informed decisions regarding cardiac support provided to patients by various blood pumps, by the positioning of the blood pumps, and by administration of pharmaceutical therapeutics. The algorithms also allow the blood pump system to determine important cardiac parameters and display them to clinicians to inform patient care decisions, or to make recommendations for modulation of support, for example by displaying a recommendation of varying levels of heart function to a clinician based on a variety of cardiac parameter inputs.

The calculation of various cardiac parameters from the blood pump function is possible based on knowledge of the blood pump operation, for example knowledge of the pressure and flow responses of the heart with regard to the blood pump operational speed and input power. Based on the operational functionality of the pump within the heart, algorithms can be constructed that calculate how cardiac metrics vary as the blood pump interacts with the cardiac system. By making these determinations and providing clinicians with immediate and historical cardiac parameters, clinicians are better able to understand and react to changes in blood pump functionality or patient cardiac health.

In particular, providing clinicians with accurate and timely cardiac parameters, such as LVEDP, LVP, aortic pulse pressure, mean aortic pressure, pump flow, pressure gradient, heart rate, cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance, enables the clinicians to make well-informed decisions about patient care. Both total and native cardiac outputs can be determined using the methods and systems described herein. The native cardiac output is used herein to describe a cardiac output of the heart alone, without the contribution of a blood pump. Similarly, the native cardiac power output is used to describe the cardiac power output of the heart without any contribution of the blood pump. The total cardiac output, in contrast, is used herein to describe the cardiac output produced by the combination of the heart and the blood pump. Similarly, the total cardiac power output is used to describe the cardiac power output of the heart including both the native power output contribution of the heart and the blood pump. Throughout this application, when cardiac power output or cardiac output is determined or calculated, the systems and methods described herein are capable of calculating either the total or the native cardiac output, and reference to cardiac output or cardiac power output may refer to either of native or total outputs.

The algorithms discussed herein enable clinicians to make informed decisions about the weaning of patients. A clinician can better determine the appropriate timing for weaning a patient from blood pump provided cardiac support based on the provided parameters. Further, the algorithms provided herein can enable clinicians to make decisions about the proper rate at which to wean a patient by providing recommendations about the level of support, motor speed, and appropriate blood pumps to provide the recommended motor speed to support the cardiac function.

The systems, devices, and methods described herein further aid in the optimization of the performance of the blood pump by the measurement and calculation of cardiac parameters. Estimations of LVP and real-time display of the LVP waveform, along with other cardiac metrics, enable a physician to understand the currently and historical cardiac function of a patient, and well as the level of support being provided by the blood pump. Using this information, physicians make determinations regarding modifications to the level of support being provided (for example, weaning a patient from support or increasing provided support), positioning and functionality of a blood pump, the occurrence of suction events, and other clinical determinations as described below.

The systems, devices, and methods described herein enable a clinician to visually determine whether the blood pump is properly positioned in the heart and functioning appropriately. The LVP estimate is very sensitive to suction events and can be employed to inform clinicians about suction events and improper positioning, and to aid in re-positioning of the pump in the heart. The cardiac metrics determined according to the algorithms described herein and displayed to clinicians can further aid in identifying the cause of suction events when they occur.

Additionally, the systems, devices, and methods described herein provide clinicians with data and recommendations to provide additional therapeutic support, such as the administration of pharmaceutical therapies to a patient to aid in the recovery of cardiac function. For example, based on cardiac parameters and trends in the parameters, the algorithms can provide recommendations as to which pharmaceutical therapies can be beneficial as well as provide dosing information. A clinician may be provided with trends in the cardiac parameters such as the native cardiac output, the end-diastolic pressure, and the cardiac power output, and based on the trends, the algorithms may make recommendations in support of the titration of inotropes.

Alternatively, a clinician may be presented with cardiac parameters to aid in the modulation of fluids and the volume status of the patient. The clinician may be provided with the native output, the end-diastolic pressure, and pulse pressure variation to enable the clinician to determine whether the patient is in an optimum fluid window, and the fluid responsiveness of the patient. The algorithm may provide a notification to the clinician indicating, based on these parameters, whether the patient is considered to be in an optimum fluid window and an indication of whether the patient is likely to be responsive to the administration of fluids.

The systems, devices, and methods described herein can be used to provide a warning to clinicians regarding predicted adverse events that are predicted based on measured and calculated cardiac parameters. Patients reliant on blood pump support are at risk for additional ischemic events. Small changes in the left-ventricular contractility, left-ventricular relaxation, and LVEDP are all early indicators of a silent ischemic event. Alerting a clinician about changes in these parameters enables clinicians to detect ischemic events earlier and to respond more quickly. Additionally, other adverse events and outcomes such as aortic regurgitation and conduction abnormalities (in the case of patients undergoing balloon aortic valvuloplasty (BAV) in preparation for a trans-catheter aortic valve replacement (TAVR)) requiring a pacemaker. Changes in left-ventricular relaxation, left-ventricular diastolic filling pressure, systolic pressure gradients, and cardiac power and total power can all function as early indicators of such an event, and may be calculated and detected by the algorithms described herein and presented to clinicians.

Finally, the systems, devices, and methods described herein can be used to balance a right-sided and left-sided device used simultaneously, for example providing bi-ventricular support, the balancing of the two devices can present a unique challenge of balancing the right and left-side devices to maintain appropriate pressures in the lungs and limit the risk of pulmonary edema. By measuring the native and total outputs along with the pulmonary artery pressure and the left-ventricular diastolic pressure, the algorithm can provide clinicians with information about these parameters to help inform decisions about the operation of the bi-ventricular devices and can provide recommendations to help the clinicians to balance the two devices.

The systems, devices, and methods presented herein describe a mechanism of measuring, in a blood pump system, based on the output of the blood pump and measured pressure signal, a variety of cardiac parameters and heart function parameters that are useful to clinicians in the care and treatment of patients being treated with cardiac support by a blood pump. The parameters and recommendations provided by the algorithm may be used by clinicians to inform a variety of medical treatment decisions, as described below.

FIG. 1 shows an exemplary prior art cardiac assist device located in a heart 102. The heart 102 includes a left ventricle 103, aorta 104, and aortic valve 105. The intravascular heart pump system includes a catheter 106, a motor 108, a pump outlet 110, a cannula 111, a pump inlet 114, and a pressure sensor 112. The motor 108 is coupled at its proximal end to the catheter 106 and at its distal end to the cannula 111. The motor 108 also drives a rotor (not visible in figure) which rotates to pump blood from the pump inlet 114 through the cannula 111 to the pump outlet 110. The cannula 111 is positioned across the aortic valve 105 such that the pump inlet 114 is located within the left ventricle 103 and the pump outlet 110 is located within the aorta 104. This configuration allows the intravascular heart pump system 100 to pump blood from the left ventricle 103 into the aorta 104 to support cardiac output.

The intravascular heart pump system 100 pumps blood from the left ventricle into the aorta in parallel with the native cardiac output of the heart 102. The blood flow through a healthy heart is typically about 5 liters/minute, and the blood flow through the intravascular heart pump system 100 can be a similar or different flow rate. For example, the flow rate through the intravascular heart pump system 100 can be 0.5 liters/minute, 1 liter/minute, 1.5 liters per minute, 2 liters/minute, 2.5 liters/minute, 3 liters/minute, 3.5 liters/minute, 4 liters/minute, 4.5 liters/minute, 5 liters/minute, greater than 5 liters/minute or any other suitable flow rate.

The motor 108 of the intravascular heart pump system 100 can vary in any number of ways. For example, the motor 108 can be an electric motor. The motor 108 can be operated at a constant rotational velocity to pump blood from the left ventricle 103 to the aorta 104. Operating the motor 108 at a constant velocity generally requires supplying the motor 108 with varying amounts of current because the load on the motor 108 varies during the different stages of the cardiac cycle of the heart 102. For example, when the mass flow rate of blood through the blood pump into the aorta 104 increases (e.g., during systole), the current required to operate the motor 108 increases. This change in motor current can thus be used to help characterize cardiac function as will be discussed further in relation to the following figures. Detection of mass flow rate using motor current may be facilitated by the position of the motor 108, which is aligned with the natural direction of blood flow from the left ventricle 103 into the aorta 104. Detection of mass flow rate using motor current may also be facilitated by the small size and/or low torque of the motor 108. The motor 108 of FIG. 1 has a diameter of about 4 mm, but any suitable motor diameter may be used provided that the rotor-motor mass is small enough, has low enough torque, and is positioned such that it is able to quickly and easily respond to changes in the physiologic pressure gradient across the pump. In some implementations, the diameter of the motor 108 is less than 4 mm.

In certain implementations, one or more motor parameters other than current, such as power delivered to the motor 108, are measured. In some implementations, the motor 108 in FIG. 1 operates at a constant velocity. In certain implementations the speed of the motor 108 is varied over time (e.g., as a delta, step, sinusoid, or ramp function) to probe the native heart function. In some implementations, the motor 108 may be external to the patient and may drive the rotor by an elongate mechanical transmission element, such as a flexible drive shaft, drive cable, or a fluidic coupling.

The pressure sensor 112 of the intravascular heart pump system 100 can be disposed at various locations on the pump, such as on the motor 108 or at the outflow of the pump, i.e. pump outlet 110. Placement of the pressure sensor 112 at the pump outlet 110 enables the pressure sensor 112 to measure the true aortic pressure (AoP), when the intravascular blood pump system 100 is positioned across the aortic valve 105. In certain implementations, the pressure sensor 112 of the intravascular heart pump system 100 can be disposed on the cannula 111, on the catheter 106, or in any other suitable location. The pressure sensor 112 can detect blood pressure in the aorta 104 when the intravascular heart pump system 100 is properly positioned in the heart 102. The blood pressure information can be used to properly place the intravascular heart pump system 100 in the heart 102. For example, the pressure sensor 112 can be used to detect whether the pump outlet has passed through the aortic valve 105 into the left ventricle 103 which would only circulate blood within the left ventricle 103 rather than transport blood from the left ventricle 103 to the aorta 104. In some implementations, the pressure sensor 112 is a fluid filled tube, a differential pressure sensor, hydraulic sensor, piezo-resistive strain gauge, optical interferometry sensor or other optical sensor, MEMS piezo-electric sensor, or any other suitable sensor.

The intravascular heart pump system 100 can be inserted in various ways, such as by percutaneous insertion into the heart 102. For example, the intravascular heart pump system can be inserted through a femoral artery (not shown), through the aorta 104, across the aortic valve 105, and into the left ventricle 103. In certain implementations, the intravascular heart pump system 100 is surgically inserted into the heart 102. In some implementations, the intravascular heart pump system 100, or a similar system adapted for the right heart, is inserted into the right heart. For example, a right heart pump similar to the intravascular heart pump system 100 can be inserted through the femoral vein and into the inferior vena cava, bypassing the right atrium and right ventricle, and extending into the pulmonary artery. Alternatively, a right heart pump can be inserted through the internal jugular vein and superior vena cava, and a left heart pump can be inserted through the axillary artery. In certain implementations, the intravascular heart pump system 100 may be positioned for operation in the vascular system outside of the heart 102 (e.g., in the aorta 104). By residing minimally invasively within the vascular system, the intravascular heart pump system 100 is sufficiently sensitive to allow characterization of native cardiac function.

Figure 2A:
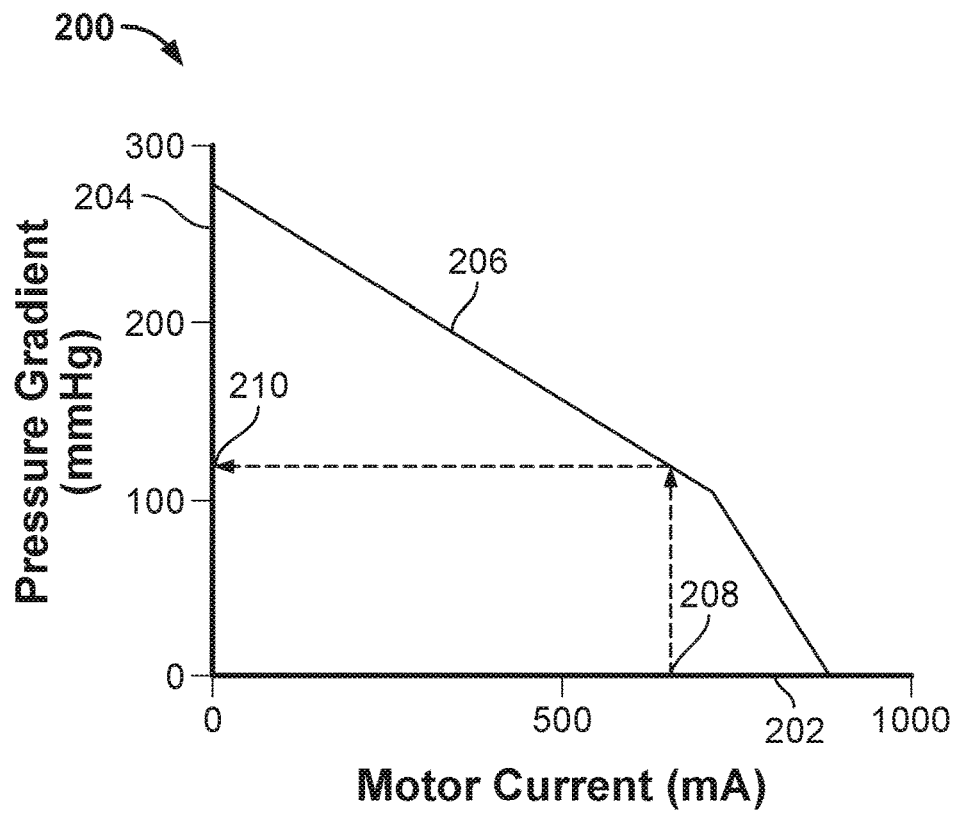
FIG. 2A shows an example plot of motor current versus a pressure gradient.

FIG. 2A shows an example plot of motor current versus a pressure gradient. The plot 200 has an x-axis 202 representing motor current in units of mA and a y-axis 204 representing a pressure gradient (dP) in units of mmHg. The plot 200 includes trend line 206 showing a relationship between the motor current and the pressure gradient. The motor current drawn by a blood pump is proportional to the pressure gradient across the blood pump cannula at a known motor speed. The plot 200 may function as a look-up for an algorithm to determine a pressure gradient from a given motor current and motor speed at which a blood pump motor is currently operating. For example, a motor current of about 650 mA indicated by point 208 on the x-axis corresponds to a pressure gradient of 120 mmHg indicated by point 210 on the y-axis, determined by extending a line up from the motor current at point 208 to the trend line 206, and then extending a line from the intersection with the trend line 206 to the y-axis at point 210. The relationship between the motor current and pressure gradient described by plot 200 may be determined in a lab for a particular blood pump under physiological conditions and may be stored in a memory of a processor within a blood pump controller.

By accessing the plot 200, a controller determines the pressure gradient associated with a motor current and motor speed at which the blood pump is currently operating. The controller can then use the pressure gradient with other determined or measured values such as the aortic pressure measured at a pressure sensor (for example, pressure sensor 112 in FIG. 1) to determine various cardiac parameters such as LVEDP, LVP, aortic pulse pressure, mean aortic pressure, pump flow, pressure gradient, heart rate, cardiac output, cardiac power output, native cardiac output, native cardiac power output, cardiac contractility, cardiac relaxation, fluid responsiveness, volume status, cardiac unloading index, and cardiac recovery index.

For example, once the pressure gradient across the blood pump cannula has been determined from the motor current and motor speed, the pressure gradient across the blood pump cannula can be used with a measured aortic pressure (such as pressure measured at the pressure sensor 112) to determine an estimation of the LVP at the inlet cage of the pump. The LVP is estimated by subtracting the pressure gradient from the aortic pressure. As described below with regard to FIG. 2B, the LVP determined in this way is a very good estimate of the actual LVP in the heart. The estimated LVP can be displayed, by the controller, on a display screen where it can be accessed and viewed by a clinician. The clinician can use the information provided by the LVP at a given moment, or a historical view of changes to the LVP, to make clinical decisions regarding the treatment of a patient including making informed decisions about changes to the support provided by the blood pump.

Although the relationship between the pressure gradient and the motor current of the blood pump at a known motor speed is depicted as a plot 200, a controller could use the information contained in the plot 200 by accessing a look-up table, or by querying a function describing the relationship between the pressure gradient and the motor current and motor speed. In some implementations, the controller may take into account additional parameters beyond the motor current and motor speed in determining the pressure gradient across the blood pump cannula, such as other properties of the pump, properties of the pump controller or console, environmental parameters, and motor speed settings. Accounting for additional parameters in the function used to determine the pressure gradient may lead to an association between the motor current and pressure differential that is more accurate, allowing for a more accurate calculation of the LVP or other cardiac parameters.

Figure 2B:
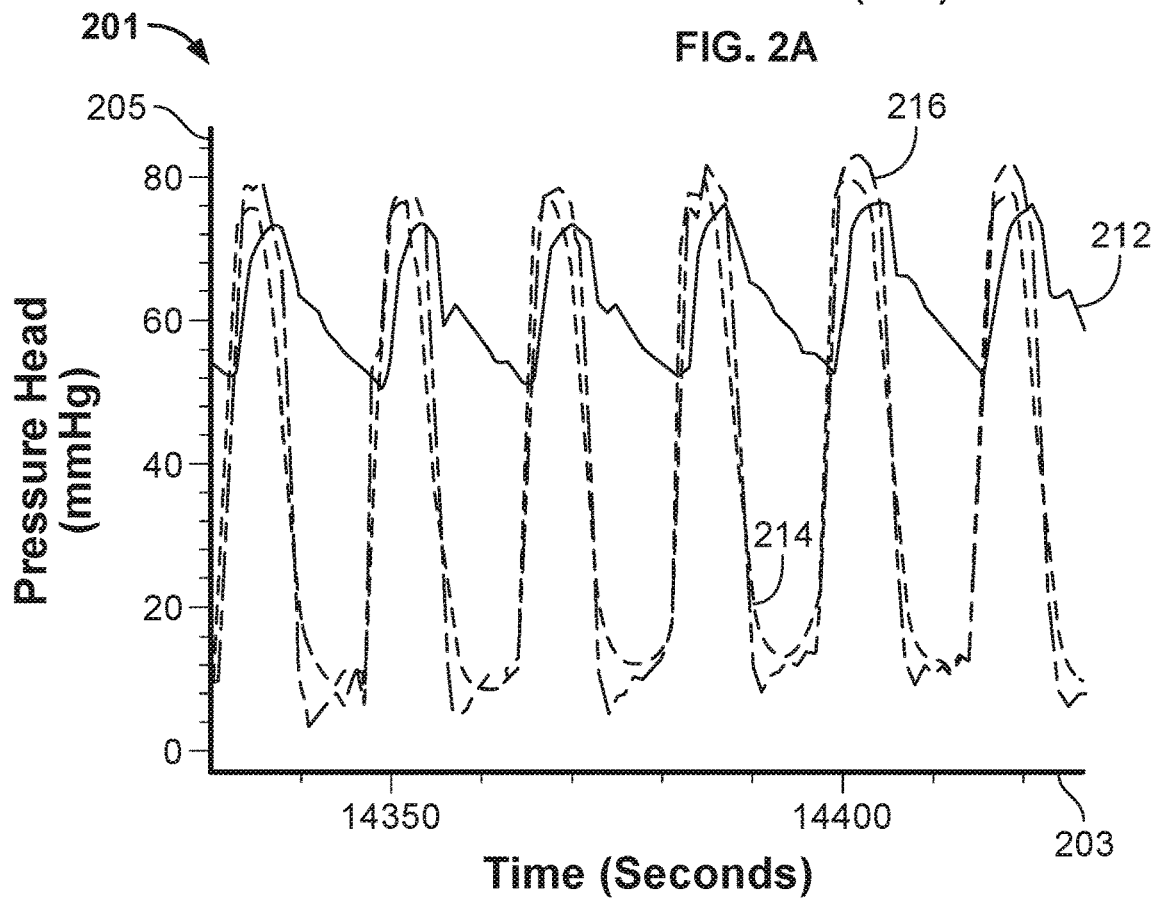
FIG. 2B shows an example plot of measured aortic pressure and calculated LVP as a function of time.

FIG. 2B shows an example plot of measured aortic pressure and calculated LVP as a function of time. The plot 201 has an x-axis 203 representing time in seconds and a y-axis 205 representing a pressure head in units of mmHg. The plot has three traces including the aortic pressure 212, the estimated LVP 214 (dotted line), and the actual measured LVP 216. The traces on the plot 201 illustrate that the estimated LVP determined from the measured aortic pressure and the determined pressure gradient across the blood pump cannula is in agreement with the measured LVP value. Based on the motor current and the measured aortic pressure, the algorithm determines continuous LVP including the full-waveform and LVEDP point within the cardiac cycle. The algorithm measures the LVP immediately inside the pump inlet 114, enabling the algorithm to determine suction events and to distinguish between systolic/continuous and diastolic/intermittent suction.

The LVEDP point in the cardiac cycle is important in the calculation of other cardiac parameters. The pressure at the end-diastole point is the LVP immediately prior to left-ventricular contraction, which can be defined by the onset of the R-wave in a reference EKG measurement. The LVEDP point in the cardiac cycle can be estimated based on the aortic pressure 212 placement signal, LVP 214 waveform and the pressure gradient at the pump. In some implementations, the LVEDP is estimated based on the identification of a peak in estimated LVP 214 waveform that is then shifted on the time axis to estimate the LVEDP point. This technique is referred to as peak detection and time indexing. In an alternative implementation, the estimated LVEDP is calculated based on a first and/or second time-based derivative of the estimated LVP 214 waveform over time.

Figure 2C:
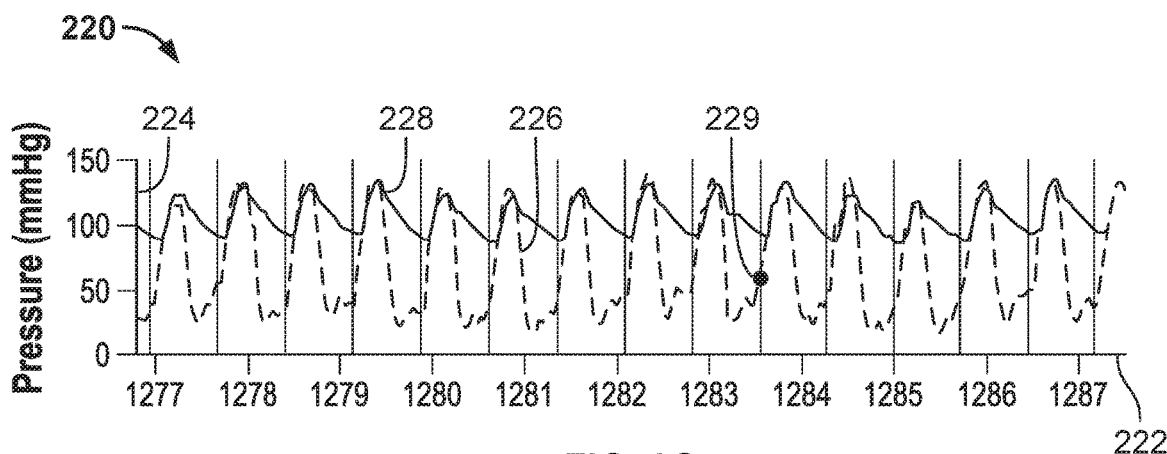
FIG. 2C shows an example plot of the LVP waveform and the aortic pressure waveform as a function of time.

FIG. 2C shows an example plot 220 of the estimated LVP 214 waveform and the aortic pressure 212 waveform with respect to time. The plot has an x-axis 222 representing time and a y-axis 224 representing pressure head in mmHg. The plot includes a trace of the estimated LVP waveform 226 (dotted line) and a trace of the aortic pressure 228 (solid line). In some implementations, the LVEDP can be selected based on the plot 220 by selecting a peak of the estimated LVP waveform 226 and shifting the point in time. Though only one LVEDP point 229 is shown in this plot 220 for convenience, the LVEDP may be calculated for each cycle of the LVP waveform to monitor changes over time.

Figure 2D:
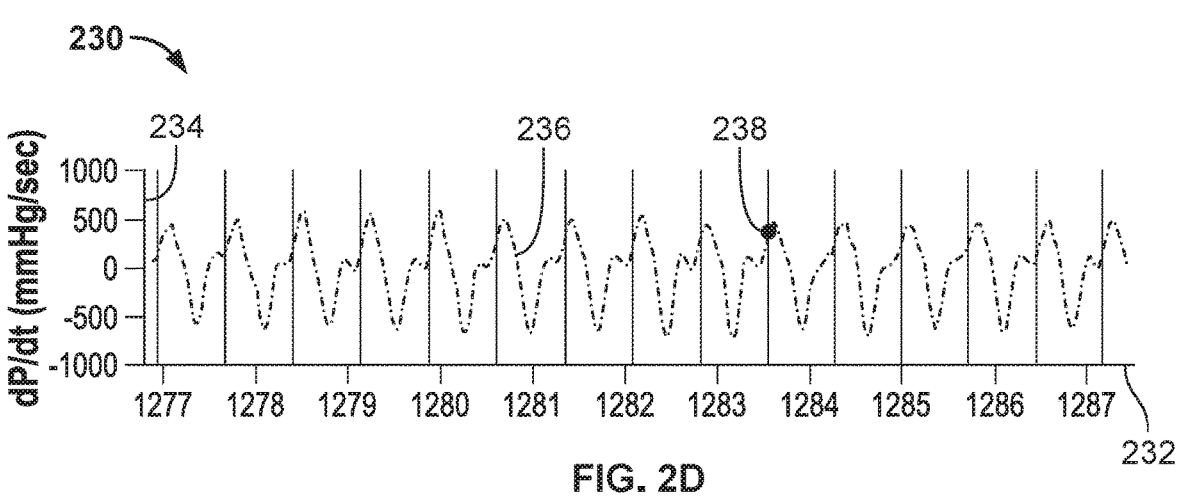
FIG. 2D shows an example plot of the first time-based derivative of the LVP wave form as a function of time.

FIG. 2D shows an example plot 230 of the first derivative of the estimated LVP 214 waveform with respect to time. The plot 230 can be calculated as a derivative of the LVP waveform 226 in plot 220. The plot 230 has an x-axis 232 representing time and a y-axis 234 representing a first derivative of pressure with respect to time (dP/dt) in mmHg/sec. The plot includes a trace of the first derivative of the LVP waveform 236, as well as an indication of the LVEDP point 238 which may be selected as the estimated LVEDP based on the trace of the first derivative of the LVP waveform 236. The point 238 shows the point associated with the LVEDP, which may be calculated, for example, as the point at which the first derivative of the LVP waveform 236 is at a time point halfway between a minimum valley and maximum peak. Though only one LVEDP point 238 is shown in this plot 230 for convenience, the LVEDP may be calculated for each cycle of the LVP waveform. Alternatively, the plot 230 of the first derivative of the LVP waveform 236 can be useful in "windowing" or narrowing a search for the LVEDP point 238 which may then be determined based on the second derivative plot or other means. The estimation of the LVEDP point 238 based on the plot 230 can be sensitive to sampling frequency with higher sampling frequency, such that higher sampling results in a more accurate calculation of the LVEDP point 238.

Figure 2E:
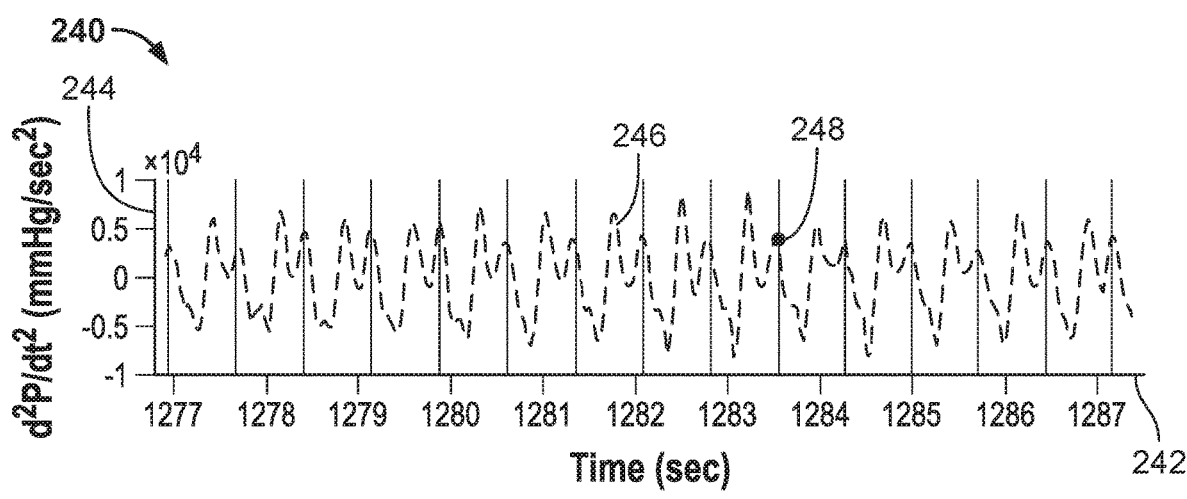
FIG. 2E shows an example plot of the second time-based derivative of the LVP wave form as a function of time

FIG. 2E shows an example plot 240 of the second derivative of the estimated LVP 214 waveform with respect to time. The plot 230 can be calculated as the derivative of the LVP waveform 236 in plot 230, or the second derivative of the LVP waveform 226 in plot 220. The plot 240 has an x-axis 242 representing time and a y-axis 244 representing the second derivative of pressure with respect to time ($d^2P/dt^2$) in mmHg/sec$^2$. The plot includes a trace of the second derivative of the LVP waveform 246, as well as an indication of the LVEDP point 248 which may be selected as the estimated LVEDP based on the trace of the second derivative of the LVP waveform 246. The point 248 shows the point associated with the LVEDP, which may be calculated, for example, as the point at which the second derivative of the estimated LVP waveform 246 has a maximum peak. Though only one LVEDP point 248 is shown in this plot 240 for convenience, the LVEDP may be calculated for each cycle of the LVP waveform. Similar to the estimation of LVEDP point 238 based on the first derivative plot 230, the estimation of the LVEDP point 248 based on the second derivative plot 240 can be sensitive to sampling frequency and is more accurate at high sampling frequencies.

The peaks of the first or second time-derivative of the LVP waveform can be used to accurately calculate the LVEDP point. Further, the peaks and valleys of the first and second time-derivatives of the LVP waveform can be used to narrow the search window for a given LVEDP point and thus improve detection of the LVEDP point, reducing false positives. Using the first or second time-based derivative of the measured aortic pressure 212 to determine the LVEDP enables the algorithm to more accurately determine the LVEDP point in the cardiac cycle. Alternatively, the aortic pressure waveform (e.g., 212 in FIG. 2B) can be similarly used with first and second derivatives of the aortic pressure waveforms to determine the LVEDP point.

Figure 3:
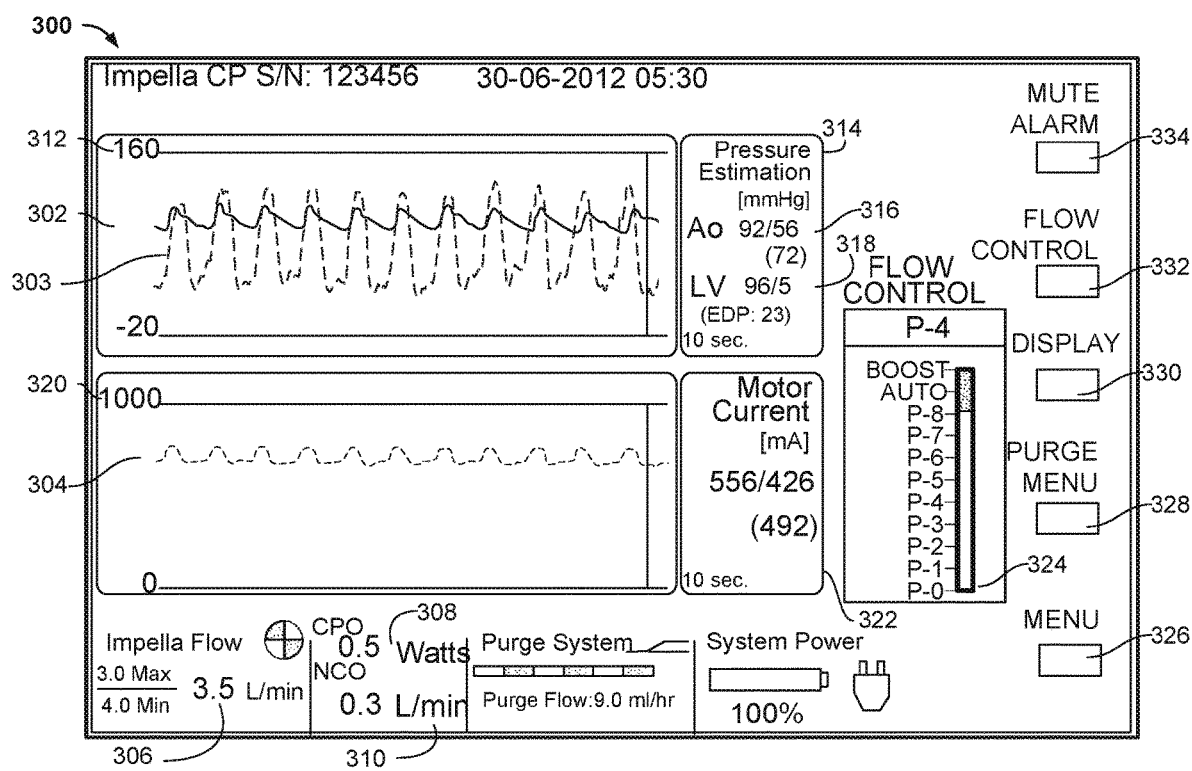
FIG. 3 shows an exemplary user interface for a heart pump controller displaying measurements over time.

FIG. 3 shows an exemplary user interface for a heart pump controller displaying a waveform of cardiac function over time. The user interface 300 may be used to control the intravascular heart pump system 100 of FIG. 1, or any other suitable heart pump. The user interface 300 includes a pressure signal waveform 302, an LVP waveform 303, and a motor current waveform 304, a flow rate 306, a measure of cardiac power output 308, and a measure of native cardiac output 310. The pressure signal waveform 302 indicates the pressure measured by the blood pump's pressure sensor (e.g., pressure sensor 112) and, when the pump is properly placed, corresponds to an aortic pressure. The pressure signal waveform 302 and the LVP waveform 303 can be used by a healthcare professional to properly place an intravascular heart pump (such as intravascular heart pump 100 in FIG. 1) in the heart. The pressure signal waveform 302 is used to verify the position of the intravascular heart pump by evaluating whether the waveform 302 is an aortic or ventricular waveform. An aortic waveform indicates that the intravascular heart pump motor is in the aorta. A ventricular waveform indicates that the intravascular heart pump motor has been inserted into an incorrect location in the ventricle. A scale 312 for the placement signal waveform is displayed to the left of the waveform. The default scaling is 0-160 mmHg. It can be adjusted in 20 mmHg increments, for example, the scale 312 is shown with scaling from −20-160 mmHg. To the right of the waveform is a display 314 that labels the waveform, provides the units of measurement, and includes an indication of the current estimated pressure. The display 314 may also include an estimation of aortic pressure 316 and/or LVP 318, which may be an instantaneous estimation, average value, or a maximum or minimum value, as well as indications of other cardiac parameters calculated from the pressure signal waveform, such as the LVEDP. In some implementations, the display 314 shows the maximum and minimum values and the average value from the calculated cardiac metrics. By including the pressure signal waveform 302, the LVP waveform 303, and the display 314, the pressure signal and LVP are displayed as a function of time and important cardiac parameters are extracted and displayed in the display 314.

In some implementations, a variability between different blood pumps is accounted for by calibrating the LVP waveform 303 to the measured aortic pressure waveform 302. The user may be prompted by the display to manually adjust the estimated LVP waveform peak (e.g., 214 in FIG. 2B) along the y-axis to coincide with the aortic pressure waveform peak (e.g., 212 in FIG. 2B). In some implementations, the calibration is automated for the user based on the pressure reading of the aortic pressure and the LVP waveforms. In other implementations, the required calibration may be calculated by a controller in the user interface 300, and a prompt with instructions to align the LVP waveform peaks during systole to the same peaks in the aortic pressure waveform may be presented to the user including a suggested value based on the controller's calculation of the same alignment in the background of the program. By calculating the alignment in the background, the controller can also detect the exact points in the cardiac cycle where the aortic pressure waveform and the LVP waveform should overlap. The overlap of the aortic pressure waveform and the LVP waveform corresponds to the aortic valve opening and aortic valve closing. These events mark the beginning and end of systole. Determination the points of overlap between the aortic pressure waveform and LVP waveform is difficult by eye, but can be calibrated by the controller to improve over calibrations that require identification of peaks of the LVP and aortic pressure waveforms.

Automating the calibration procedure simplifies the use of the user interface 300 and ensures appropriate calibration values are presented to the user. The calibration calculations can be further improved at high sampling frequencies.

The motor current waveform 304 is a measure of the energy intake of the heart pump's motor. The energy intake varies with the motor speed and the pressure difference between the inlet and outlet areas of the cannula resulting in a variable volume load on the rotor. When used with an intravascular heart pump (such as intravascular heart pump 100 in FIG. 1), the motor current provides information about the catheter position relative to the aortic valve. When the intravascular heart pump is positioned correctly, with the inlet area in the ventricle and the outlet area in the aorta, the motor current is pulsatile because the mass flow rate through the heart pump changes with the cardiac cycle. When the inlet and outlet areas are on the same side of the aortic valve, the motor current will be dampened or flat because the inlet and outlet of the pump are located in the same chamber and there is no variability in differential pressure resulting in a constant mass flow rate, and subsequently constant motor current. A scale 320 for the motor current waveform is displayed to the left of the waveform. The default scaling is 0-1000 mA. The scaling may be adjustable in 100 mA increments. To the right of the waveform is a display 322 that labels the waveform, provides the units of measurement, and shows the maximum and minimum values and the average value from the samples received. Though the pressure sensor and motor current sensor may not be required for positioning of surgically implanted pumps the sensors can be used in such devices to determine additional characteristics of native heart function to monitor therapy.

While only the three waveforms are shown in FIG. 3 (pressure signal waveform 302, LVP waveform 303, and the motor current waveform 304) additional waveforms may be displayed on the main screen of the display 300 or accessible on additional screens. For example, a contractility waveform, a cardiac state waveform, an ECG waveform, or any other appropriate cardiac parameter which changes with time or pulse can be displayed on display 300. The display of cardiac information as a trend line allows a physician to view the historical cardiac state of a patient and to make decisions based on the visible trends. For example, a physician may observe a decline or increase in the aortic pressure displayed in the pressure signal waveform 302 over time and determine to alter or continue treatment based on this observation.

The position, depictions of the metrics on the controller, and the identification and number of metrics and recommendations in FIG. 3 are meant to be illustrative. The number of metrics and indicators, position of same metrics and indicators on the console and the metrics displayed may be varied from those shown here. The cardiac parameters displayed to a user can be, for example, LVEDP, LVP, aortic pulse pressure, mean aortic pressure, pump flow, pressure gradient, heart rate, cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. In some implementations, the font, font size, layout, and positioning of the data displayed to a user may be configured for ease of use in a critical care setting.

The measure of the measure of native cardiac output 310 includes a display of a NCO in L/min calculated based on the measured cardiac parameters. The native cardiac output is a measure of the blood flow attributed to the heart itself, or the rate of blood flow in the vasculature surrounding the blood pump. The native cardiac output is calculated from the placement signal (Aortic Pressure) 316 and the pulse pressure calculated at the controller by subtracting the minimum aortic pressure value from the maximum aortic pressure value. The pulse pressure may be calculated by the controller periodically. The native cardiac output can be used to calculate additional cardiac parameters of clinical relevance. For example, the native cardiac output can be used in conjunction with information about the flow rate of the blood pump to calculate a total cardiac output of the heart itself and the blood pump.

The measure of cardiac power output 308 includes a display of a total cardiac power output in Watts calculated based on the measured cardiac parameters. The total cardiac power output is calculated from the total cardiac output, calculated based on the native cardiac output as described above. The total cardiac power output is calculated by multiplying the cardiac output by the mean arterial pressure and dividing by 451.

The flow rate 324 can be a target blood flow rate set by the user or an estimated actual flow rate. In some modes of the controller, the controller will automatically adjust the motor speed in response to changes in afterload to maintain a target flow rate. In some implementations, if flow calculation is not possible, the controller will allow a user to set a fixed motor speed indicated by speed indicator.

A memory within the user interface or controller records the data measured, calculated and displayed on the controller. The memory may have a sampling rate of 25-150 Hz. In some implementations, a higher sampling rate, such as 100 Hz or greater, is preferable as the data will be recorded in a data log in the memory at a faster rate. The higher fidelity data recorded in the memory can be used to better estimate cardiac function over time. The waveforms, algorithms, and alarms displayed to the user on the user interface may be displayed at a lower rate for efficiency.

The display 300 includes various buttons 326-334 to access additional display screens. The buttons include a menu button 326, purge menu button 328, display button 330, flow control button 332, and mute alarm button 334. The buttons shown on display 300 are meant to be illustrative, and alternate or additional buttons may be accessible to a user. The menu button 326 may allow a user to access additional information about the use of the display 300, including software version, registrations, and dates of use. The menu button 326 may also allow a user to access options such as the power mode of the display 300 or locking the display 300. The menu button 326 may also allow a user to calibrate the display 300 or allow a user to access options or instructions for the calibration of the display 300 in conjunction with an attached blood pump. For example, a user may calibrate a measured pressure value or a cardiac parameter displayed as a waveform to a known value of the cardiac parameter measured by an arterial catheter or similar. The purge menu button 328 may allow a user to access additional use options, settings, and information related to the purge system of an attached blood pump. The display menu button 330 may allow a user to access additional cardiac metrics and parameters and in some cases to add or change the cardiac metrics displayed on the main screen of the display 300. The flow control button 332 allows a user to access additional options and settings related to controlling the flow rate of the pump by adjusting the pump motor speed. The flow control button may allow the user to access recommendations related to the current pump motor speed and various cardiac metrics calculated by the controller and may allow a user to input or accept adjustments to the pump motor speed. The mute alarm button 334 may allow a user to silence an alarm or to access additional information about an alarm or warning given by the controller. The controller may issue warning notifications to a user regarding the use of the display, blood pump and related systems, or the cardiac metrics calculated by the controller. The warnings and alarms may be audible alarms, pop-up screens on the display 300, or may be sent directly to a clinician, for example through a text, page, or email.

In some implementations, the warnings or alarms are triggered by a cardiac metric calculated, measured or monitored by the controller falling below a set threshold value. In some implementations, the warnings or alarms are triggered by a cardiac metric calculated, measured or monitored by the controller exceeding a set threshold value. In some implementations, the warnings or alarms are triggered by a change in a cardiac metric calculated, measured or monitored by the controller exceeding or falling below a set threshold value. In some implementations, the set threshold value is a system value set within the controller. In some implementations, the set threshold value is set by a clinician based on a patient's history and health. In some implementations, the set threshold value is a previous value of the cardiac metric, for example, a previous value measured or calculated a predetermined amount of time before.

In some implementations, the warnings or alarms are recommendations for altering the support provided to the heart by the blood pump based on one or more of the calculated, measured, or monitored cardiac metrics. FIGS. 4-11 illustrate processes by which the controller determines various recommended changes to the cardiac support provided by the blood pump.

Figure 4:
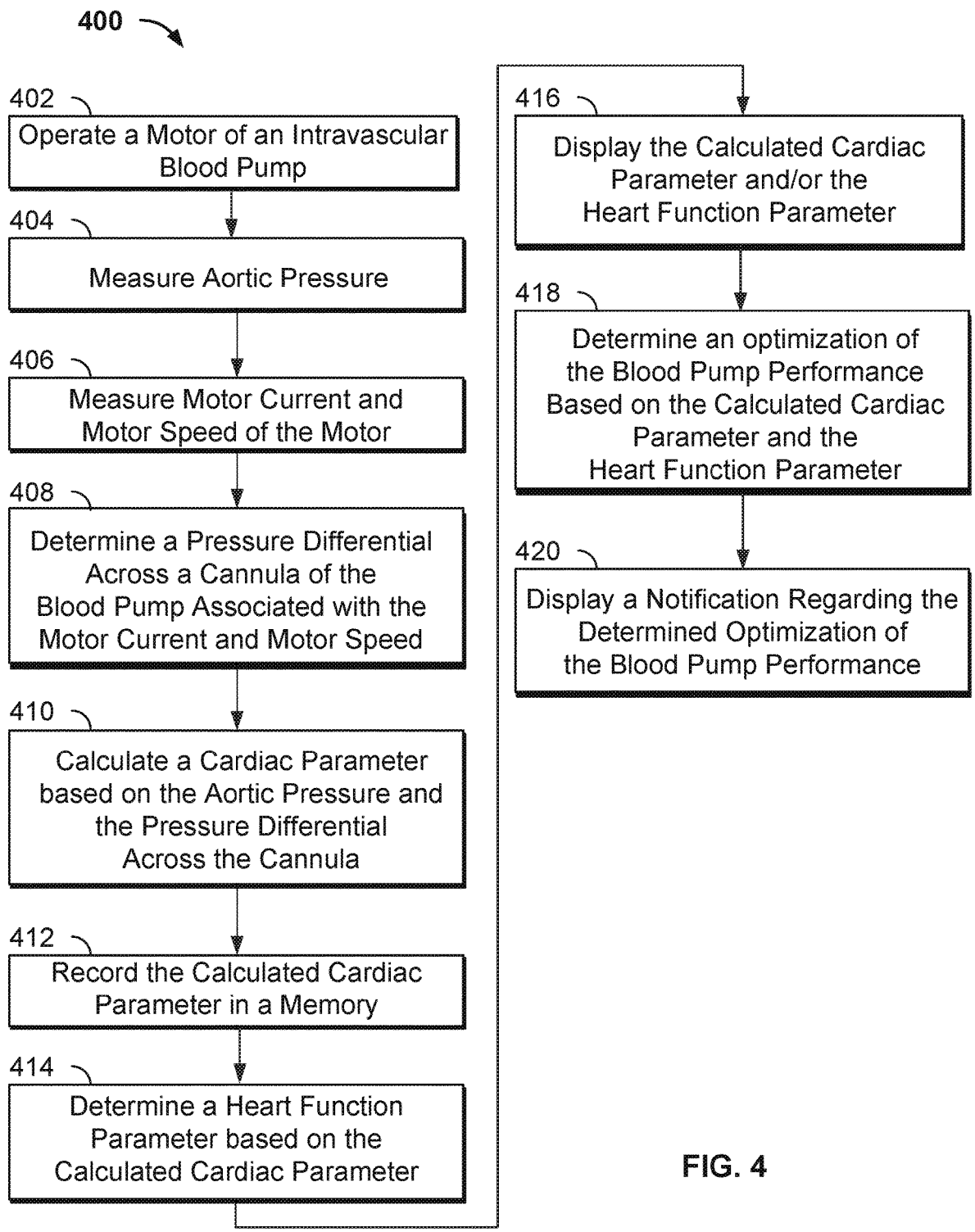
FIG. 4 shows a process for optimizing the performance of a blood pump in the heart based on measured and calculated cardiac parameters.

FIG. 4 shows a process 400 for optimizing the performance of a blood pump in the heart based on measured and calculated cardiac parameters.

In step 402, the motor of a heart pump is operated at a rotational speed. In step 404, the aortic pressure is measured. The aortic pressure may be measured by a pressure sensor coupled to the heart pump, by a separate catheter, by a noninvasive pressure sensor, or by any other suitable sensor. The pressure sensor may be a fluid-filled tube, a differential pressure sensor, hydraulic sensor, piezo-resistive strain gauge, optical interferometry sensor or other optical sensor, MEMS piezo-electric sensor, or any other suitable sensor. In some implementations, ventricular pressure is measured in addition to or in alternative to measuring aortic pressure. In step 406, the current delivered to the motor is measured and the motor speed is measured. In step 408, the pressure differential across a cannula of the blood pump is determined based on the measured motor current and the motor speed, by using a lookup table or accessing a function that accounts for the measured motor current at the known speed, and optionally other parameters. In step 410, a cardiac parameter is calculated based on the pressure differential across the cannula of the blood pump and the aortic pressure. The cardiac parameter may be one of a LVEDP, LVP, aortic pulse pressure, mean aortic pressure, pump flow, pressure gradient, or heart rate. These cardiac parameters can each be used by clinicians as a measure of various aspects of cardiac health and function. The trends of each of the cardiac parameters over time can be used by a clinician to determine if the native heart output is improving or declining and can make clinical decisions about the support being provided by the blood pump and pharmaceutical therapies based on these trends. In some implementations, more than one cardiac parameter is calculated based on the pressure differential across the cannula of the blood pump and the aortic pressure.

In particular, in order to evaluate the performance of the blood pump within the heart of a patient, one or more of the LVP and LVEDP may be calculated according to the algorithm. In some implementations, the calculated metrics are evaluated by the processor to determine whether there are problems with a current performance of the blood pump and to offer suggestions to the user to correct the problems. In some implementations, the metrics are presented for evaluation by a health care professional.

In step 412, the calculated cardiac parameter is recorded in the memory. By accessing the recorded cardiac parameters stored in the memory, a historical view of the cardiac parameter over time can be accessed by a user or displayed on a display console as a trend line.

In step 414, a heart function parameter is determined based on the calculated cardiac parameter. The heart function parameter can be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. These heart function parameters can be calculated from the calculated cardiac parameter and other available measured parameters. The heart function parameters offer additional information to clinicians about the heart function, as well as the performance of the blood pump in relation to the cardiac function. In some implementations, the heart function parameter is also recorded in the memory in order to provide historical data and heart function parameter trends with respect to time. In some implementations, more than one heart function parameter is determined.

For example, cardiac output may be calculated based on the motor current and motor speed of the blood pump and the measured aortic pressure. From the aortic pressure, the pulse pressure of the aortic waveform can be derived. In implementations in which the pressure sensor (e.g., pressure sensor 112 in FIG. 1) is located at the pump outflow, the aortic pressure, and the pulse pressure of the aortic waveform, is measured at the aortic root where it is less influenced by aortic and systemic resistance and systemic vascular compliance as compared to peripheral approaches to calculate the pulse pressure (for example, PiCCO, Edwards FloTract). In some implementations, the pulse pressure, and accordingly the algorithm calculation, is influenced by the aortic compliance at the point of measurement, which varies from patient to patient. However, the patient-to-patient variance can be accounted for by calibrating the cardiac output algorithm, and the aortic compliance should only minimally vary within a patient over the duration of support, as aortic root wall properties are not typically impacted by vasoactive and inotropic drugs. Other cardiac output algorithms which rely on pulse pressure and derivative of the pulse pressure wave (e.g., PiCCO, FloTract, or PulseCo) cannot discern the pulsatility due to the native heart from the pulsatility due to the support device. In contrast, the algorithm is able to discern native and pump-driven pulsatility and de-couple changes in pulsatility due to changes in flow from either the pump or the heart.

In step 416, the calculated cardiac parameter and/or the heart function parameter is generated for display and is displayed to a user on a display interface. The calculated cardiac parameter can be accessed in the memory of the controller and processed to ready the cardiac parameter for display as a number, a waveform over time, or as a maximum or minimum value. The cardiac parameter and heart function parameter can be displayed to a clinician, for example a lab technician or nurse in an intensive care setting or a catheterization lab, on a display, such as display 300 in FIG. 3. The calculated cardiac parameter, the heart function parameter, and optionally the historical views of the cardiac parameter and/or heart function parameter over time, allows a clinician to view and make decisions based on the trends of the cardiac parameter and heart function parameter. An example of user interface is shown in FIG. 5 to illustrate the use of the algorithms derived by the algorithm in determining a correct position of the blood pump.

The display and/or the determination of the cardiac parameter and heart function parameter can be continuous or nearly continuous while the heart pump is implanted in the heart. This can be advantageous over conventional catheter-based methods that only allow sampling of cardiac function at specific times during the cardiac cycle or at discrete points in time. For example, continuous monitoring of the cardiac parameter may allow more rapid detection of cardiac deterioration. Continuous monitoring of the cardiac parameter and heart function parameter can illustrate changes in the heart condition over time. Additionally, if the cardiac assist device is already in the patient, the cardiac function can be measured without having to introduce an additional catheter into a patient. The cardiac parameter and/or heart function parameter may be displayed as shown in the user interface of FIG. 3 or using any other suitable user interface or report.

In step 418, an optimization of the blood pump performance is determined based on the calculated cardiac parameter and heart function parameter. The controller may access the calculated cardiac parameter in the memory and compare the calculated cardiac parameter or the heart function parameter to a stored threshold value in order to determine the blood pump performance can be optimized with regard to the cardiac function of the patient. For example, the controller may determine that the patient cardiac function is improving, and the patient can be weaned from blood pump support. Alternatively, the controller can determine that the patient cardiac function is declining and the blood pump support provided to the patient should be increased. Additionally or alternatively, the controller can determine that there is a suction risk or a suction event based on current placement of the blood pump, and that the position of the blood pump can be optimized. The threshold value to which the calculated cardiac parameter or heart function parameter is compared may be pre-set at manufacture, set by the physician via the user interface, or be based on a previous reading of the calculated cardiac parameter and heart function parameter of the patient. For example, the controller may compare a calculated LVP to a threshold value to determine that there is a suction risk due to current positioning of the blood pump. In some implementations, the controller compares a LVP waveform to one or more a stored waveforms. In some implementations, the controller compares minimum and/or maximum points from a LVP waveform to stored threshold values.

In step 420, a notification regarding the determined optimization of the blood pump performance is generated and displayed. The notification can be accessed in from a memory in the controller and according to the determined optimization and generated for display. The notification regarding the optimization of blood pump performance can be displayed in the user interface of FIG. 3. In some implementations, the notification regarding the optimization of the blood pump performance is displayed on the main screen. In some implementations, the notification regarding the optimization of the blood pump performance is displayed as a pop-up or warning. The notification may suggest that blood pump motor speed be increased or decreased, or may indicate that there is a positioning problem or risk of a suction event. In some implementations, the notification may further indicate a recommendation for addressing a positioning issue or suction event, for example by recommending that the blood pump motor speed by increased or decreased, or that the blood pump be moved in a particular direction by a certain distance. In some implementations, the recommended change in motor speed may exceed a speed of a currently used blood pump, and the notification may recommend changing the blood pump type.

In some implementations, the displayed notification is interactive and the controller can take action with regard to recommended changes in motor speed based on an input from a clinician. In other implementations, the notification may indicate that the recommended change in motor speed has already been automatically made by the controller.

Figure 5A:
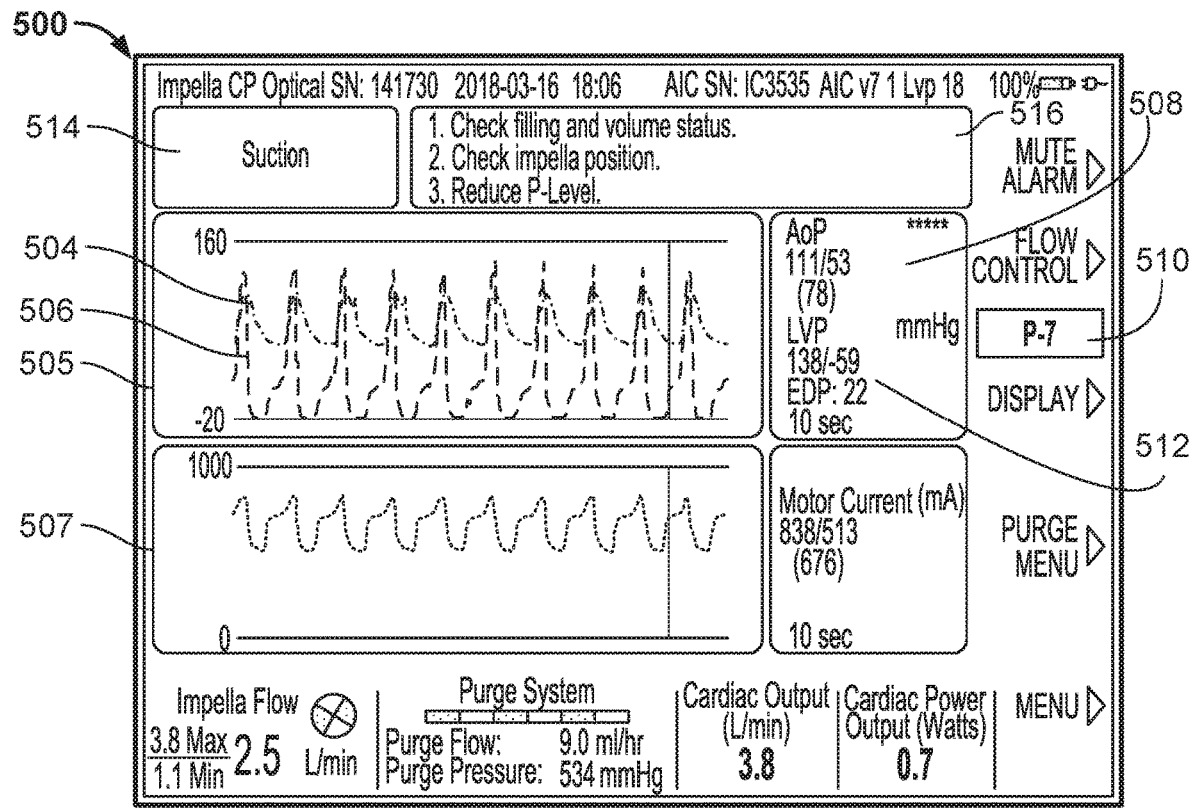
FIG. 5A shows an exemplary user interface for a heart pump controller illustrating an intermittent suction event at the blood pump.

FIG. 5A shows a user interface 500 for a heart pump controller illustrating an intermittent or diastolic suction event at the blood pump. The user interface 500 includes components similar to the user interface 300, and not all components are labelled or displayed here for simplicity. The user interface 500 includes a first plot 505 showing an aortic pressure waveform 504 and a LVP waveform 506, and a second plot 507 showing a motor current waveform. The user interface also includes an indication of aortic pressure 508 over the aortic pressure waveform 504 including a minimum and maximum value, an indication of LVP 512 over the LVP waveform 506 including a minimum and maximum value. An indication of current motor speed 510, a warning pop-up 514, and instructions or recommendations for addressing the warning pop-up 516 are also included in the user interface 500.

The aortic pressure waveform 504 and LVP waveform 506 measured by the controller based on pressure readings and motor current of the blood pump are helpful in detecting diastolic and intermittent suction events at the blood pump caused by insufficient blood volume in the heart. During such suction events, the LVP waveform 506 falls below zero in the first plot 505 in early diastole but recovers by the end diastolic pressure point. The systolic phase of the LVP waveform 506 is normal. These events may also be detected by the indication of LVP 512 and indication of aortic pressure 508, as the maximum indication of LVP 512 is typically normal and greater than the maximum indication of aortic pressure 508, while the minimum indication of LVP 512 is abnormal and is very low or less than zero during intermittent and diastolic suction events. Accordingly, the minimum value of the indication of LVP 512 provides an early indicator of diastolic suction. The controller can issue a warning 514 based on a comparison of the minimum value of the indication of LVP 512 to a threshold value, for example, 0 mmHg, −10 mmHg, −20 mmHg, −30 mmHg, −40 mmHg, or any other suitable threshold value. In some implementations, the comparison of the minimum value of the indication of LVP 512 may be used to determine a level of risk or severity of the suction event, for example with 0 mmHg signifying a borderline or low risk, −10 mmHg signifying a mild suction risk, −20 mmHg signifying a moderate risk of suction, etc. The controller can further provide recommendations 516 to a physician, nurse, or technician for how to react to the warning 514 to address and correct the suction event. For example, the controller may provide a recommendation to check additional cardiac metrics to determine a cause of the suction event or check on patient health before adjusting the positioning or cardiac support level of the blood pump. The controller may also provide instructions or recommendations to check the positioning of the blood pump based on the suction event detection and further may recommend a change in the level of support provided by the blood pump by a change to the motor current 510.

Figure 5B:
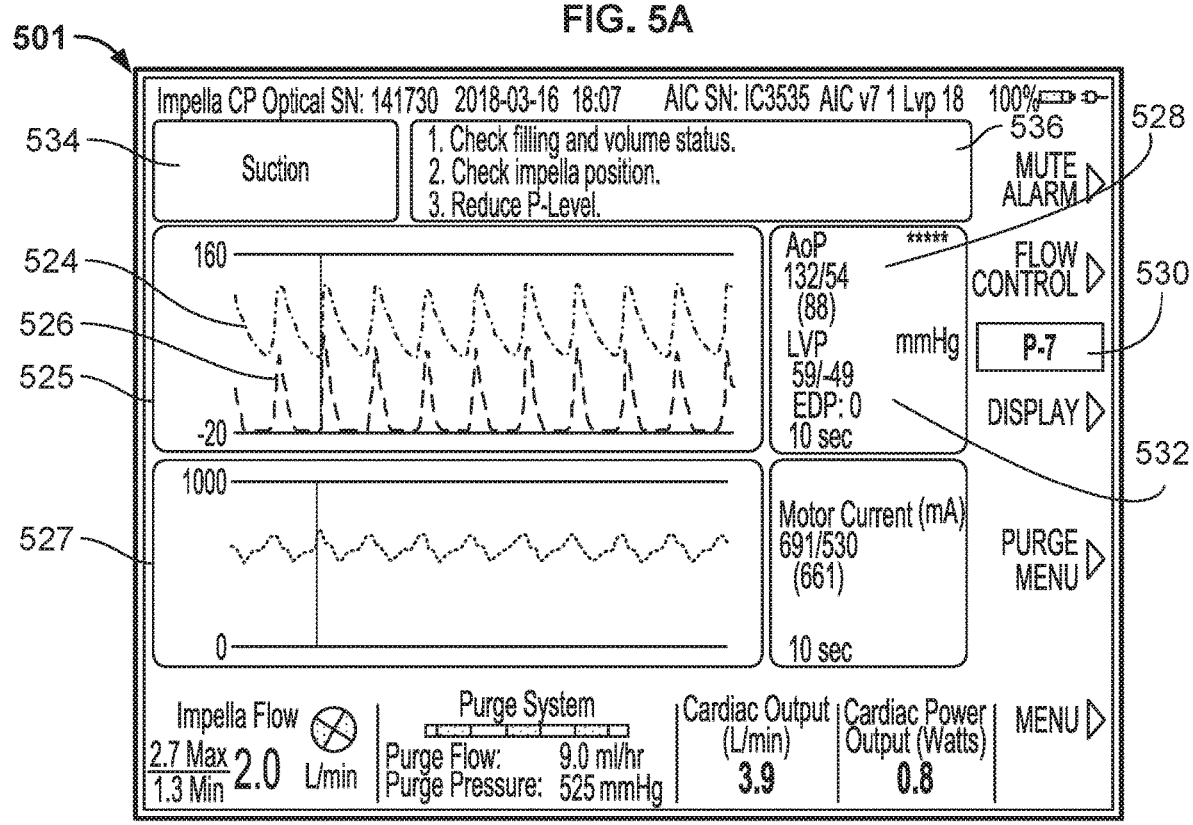
FIG. 5B shows an exemplary user interface for a heart pump controller illustrating a continuous suction even at the blood pump.

FIG. 5B shows a user interface 501 for a heart pump controller illustrating a continuous suction even at the blood pump. Like the user interface 500 in FIG. 5A, the user interface 501 includes components similar to the user interface 300, and not all components are labelled or displayed here for simplicity. The user interface 501 includes a first plot 525 showing an aortic pressure waveform 524 and a LVP waveform 526, and a second plot 527 showing a motor current waveform. The user interface also includes an indication of aortic pressure 528 over the aortic pressure waveform 524 including a minimum and maximum value, an indication of LVP 532 over the LVP waveform 526 including a minimum and maximum value. An indication of current motor speed 530, a warning pop-up 534, and instructions or recommendations for addressing the warning pop-up 536 are also included in the user interface 501.

Similar to the process by which intermittent (diastolic) suction events are determined and shown by the displayed LVP and aortic pressure in FIG. 5A, the determination of continuous or systolic suction events is informed by the LVP waveform 526 and aortic pressure waveform 524, indication of LVP 528, and indication of aortic pressure 532. By displaying these and other cardiac metrics to a user via the user interface 501, a user such as a clinician or physician can be aware of continuous suction events and can appropriately react to address them. Continuous suction events are typically caused by poor positioning of the blood pump or a cardiac structure blocking the blood pump inflow (e.g., pump inlet 114). During a continuous suction event, the LVP waveform 526 falls below zero during diastole and never rises above the aortic pressure waveform 524 during systole. Additionally, during a continuous suction event the maximum value of the indication of LVP 532 is abnormal and is typically much lower than a maximum value of the indication of aortic pressure 528, while the minimum value of the indication of LVP 532 is abnormal and is less than zero. The LVEDP calculated from the LVP waveform 526, if displayed, is equal to zero.

As in the case of the intermittent (diastolic) suction event of FIG. 5A, a warning 534 and recommendations 536 may be displayed when a continuous suction event is detected. The recommendations 536 displayed when a continuous suction event is detected may be the same or different from the recommendations 516 displayed during an intermittent suction event.

Figure 5C:
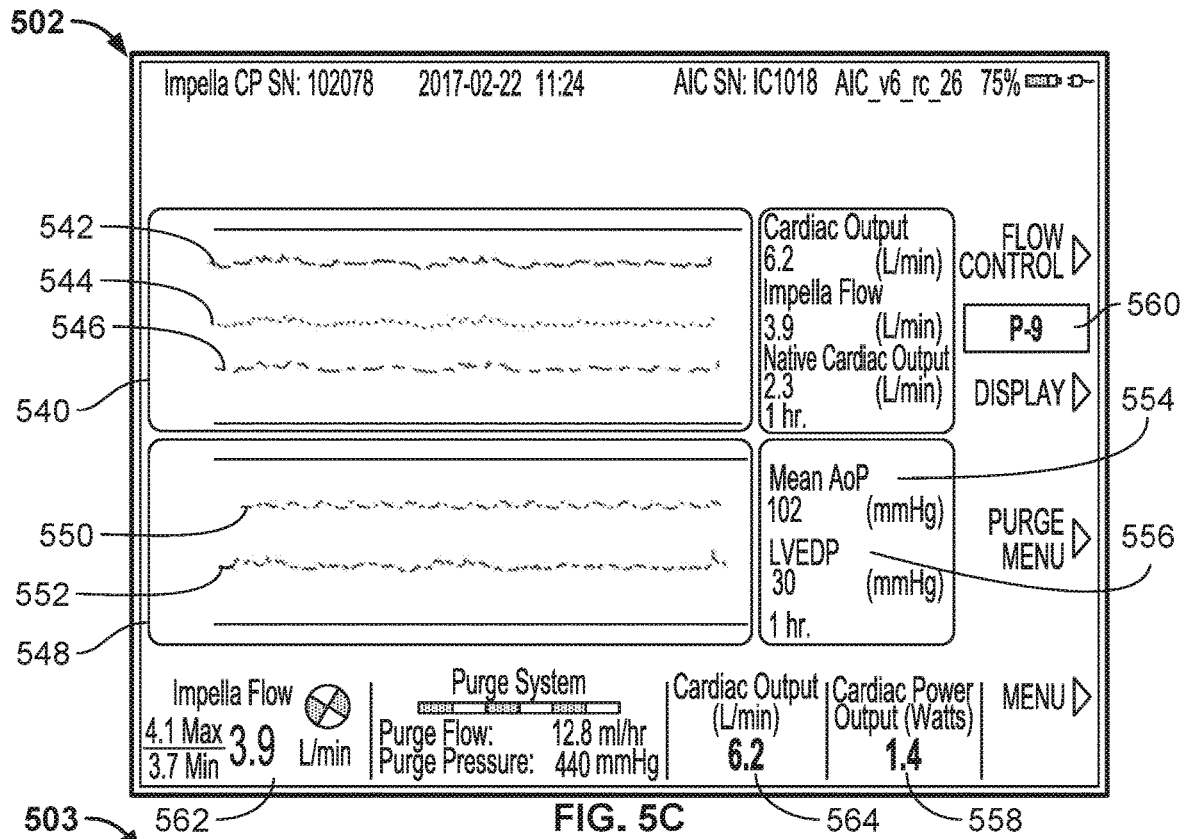
FIG. 5C shows an exemplary user interface for a heart pump controller illustrating a metric trend screen.

FIG. 5C shows a user interface 502 for a heart pump controller illustrating a metric trend screen. The trend screen includes a first plot 540 displaying a cardiac output trend waveform 542, a blood pump flow trend waveform 544, and a native cardiac output trend waveform 546, as well as associated values of cardiac output, blood pump flow, and native cardiac output for rapid assessment by a physician. The user interface 502 metric trend screen also includes a second plot 548 displaying a mean aortic pressure trend waveform 550, and an LVEDP trend waveform 552, as well as associated values of mean aortic pressure 554 and LVEDP 556. The user interface 502 also includes an indication of motor speed of a blood pump 560, blood pump flow 562, cardiac output 564, and cardiac power output 558.

The metric trend screen of the user interface 502 is accessible to a physician to further illustrate the historic data associated with various cardiac parameters over time. Such historic data can help physicians to understand the progress of the patient's cardiac health as well as to identify events taking place. For example, the metric trend screen of the user interface 502 shown in FIG. 5C displays cardiac output trend waveform 542, blood pump flow trend waveform 544, native cardiac output trend waveform 546, aortic pressure trend waveform 550, and a LVEDP trend waveform 552 all of which are relatively stable over time. However, changes or trends in these waveforms over time can indicate suction events or risk of suction. The LVEDP trend waveform 552 should be stable over the course of providing cardiac support to the patient. A low and/or declining LVEDP trend waveform 552 indicates that there is an increasing risk of diastolic suction. Having this waveform readily available to a physician enables the physician to monitor the risk of suction events. In order to determine a cause of the suction, a physician can consult the metric trend screen of the user interface 502, where an LVEDP trend waveform 552 that is high but abruptly drops to zero implies a continuous or systolic suction event, while a low LVEDP trend waveform 552 that hovers around 0 implies an intermittent or diastolic suction event. The display of these trends and values is made possible by the calculation of the metrics by the controller algorithm from the blood pump motor current and aortic pressure, and physicians are able to make informed decisions about patient care based on the values and trends.

Beyond merely providing indications of suction events, the display of various waveforms and average cardiac metric values can also provide information to physicians that enable them to determine a positioning error of the blood pump. For example, by observing changes in the LVP waveform (e.g., 506 in FIG. 5A or 526 in FIG. 5B) with respect to the aortic pressure waveform (e.g., 504 in FIG. 5A or 524 in FIG. 5B) a physician or technician can determine that a blood pump has migrated into the left ventricle and is no longer providing appropriate support as a result. When a blood pump migrates into the left ventricle, a change in the shape of the LVP waveform provides instant feedback that the positioning error has occurred. A comparison of the LVP maximum and minimum values to the aortic pressure maximum and minimum values can indicate to the physician that the aortic pressure values have begun to reflect a left-ventricular signal instead of the aortic pressure. Meanwhile the LVEDP remains stable, confirming that there are no ventricular structures impairing the flow area despite the migration of the pump.

The display of the waveforms can also be useful during a repositioning of a pump that has migrated into the left ventricle. The separate LVP and aortic pressure waveforms can be viewed to confirm a distinct aortic pressure signal and can provide instantaneous feedback to the physician or technician during repositioning. Comparison of the LVP indication and the aortic pressure indication can also be viewed and can confirm that repositioning of the blood pump as the aortic pressure values separate from the LVP values.

In addition to displaying the waveforms and cardiac metric values, the user interface may provide a warning and/or recommendations if a blood pump positioning problem is detected. The recommendations may include suggestions to decrease a pump flow rate or motor speed and to access a repositioning guide.

Figure 5D:
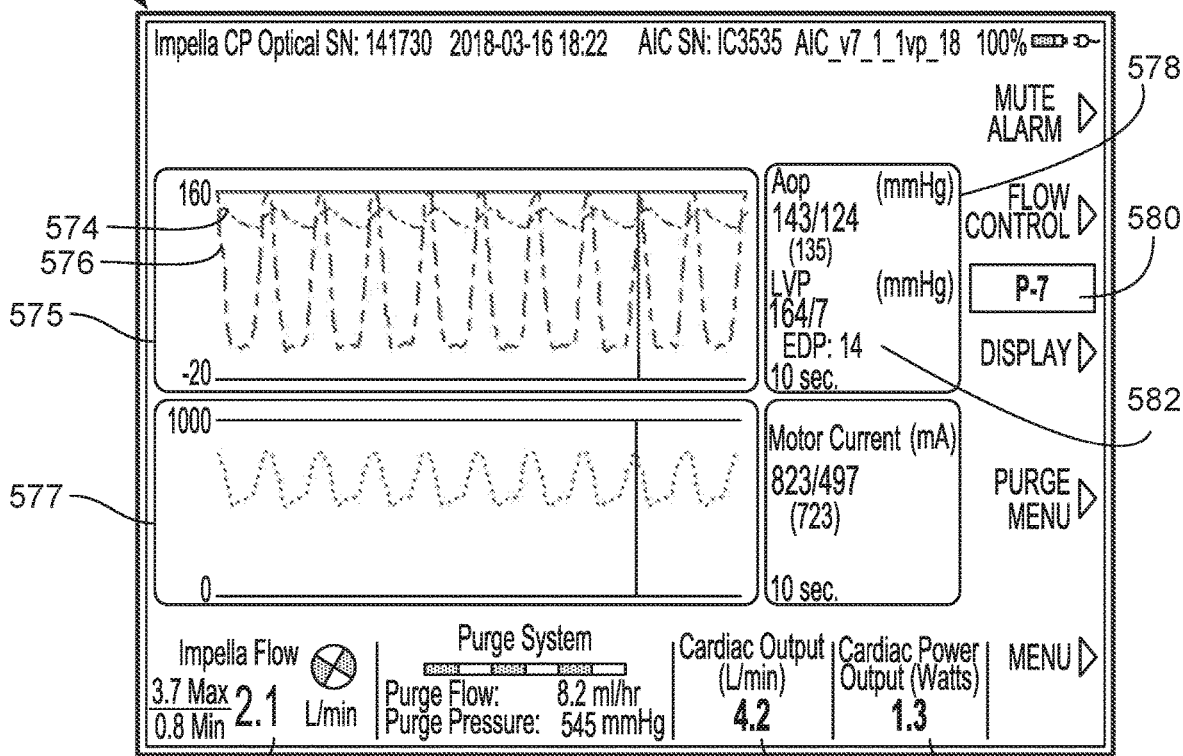
FIG. 5D shows an exemplary user interface for a heart pump controller illustrating changes in heart function during weaning as captured by the displayed metrics.

In addition to displaying cardiac waveforms and values that can indicate to physicians about suction events and positioning problems, the calculated cardiac parameters and metrics can also inform weaning decisions. FIG. 5D shows a user interface 504 for a heart pump controller illustrating changes in heart function during weaning as captured by the displayed metrics. The user interface includes a first plot 575 showing an aortic pressure waveform 574 and a LVP waveform 576, and a second plot 577 showing a motor current waveform. The user interface also includes an indication of aortic pressure 578 over the aortic pressure waveform 574 including a minimum, maximum, and mean value, and an indication of LVP 582 over the LVP waveform 576 including a minimum, maximum, and end-diastolic (LVEDP) value. An indication of current motor speed 580, an indication of blood pump flow rate 588, an indication of cardiac output 586, and an indication of cardiac power output 584 are also included in the user interface 504.

The LVP waveform 576 and aortic pressure waveform 575 displayed in FIG. 5D are illustrative of a recovered patient with stable hemodynamics. The LVEDP should be stable during weaning process, as the native heart takes over function and clears excess left-ventricular volume. The cardiac output should similarly be stable during weaning as the native heart takes over for the pump output, and the cardiac power output should be stable and preferably within the range required by decision protocols of the specific institution. The progress of a recovered patient during weaning can also be visualized on the metric trend screen, where an increase in the native cardiac output (e.g., 546 in FIG. 5C) occurs with decreasing blood pump flow (e.g., 544 in FIG. 5C) as the support from the blood pump is decreased over time. The native heart takes over the function from the blood pump during the weaning process, and the cardiac output (e.g., 542 in FIG. 5C) remains stable. The LVEDP (e.g., 552 in FIG. 5C) is stable or declining as the native heart takes over. Finally, the cardiac power output (e.g., 558 in FIG. 5C) is stable.

In the case of a patient with a worsening condition, the LVEDP is likely to rise during a weaning attempt, as the heart is unable to pump the excess blood volume and the left-ventricular volume increases. The LVP waveform 576 and aortic pressure waveform 574 may decrease during this time. The cardiac output 586 and cardiac power output 584 also decrease during weaning of a sick patient as the native heart fails to compensate for the decreased support from the blood pump. The declining function of a sick patient during weaning can also be visualized on the metric trends screen, where the native cardiac output (e.g., 546 in FIG. 5C) may decline over time as the patient becomes more dependent on the blood pump support. The LVEDP waveform (e.g., 552 in FIG. 5C) may rise as the heart is unable to pump the blood and the LVP increases. The cardiac power output (e.g., 558 in FIG. 5C) decreases with lower total power output.

Figure 6:
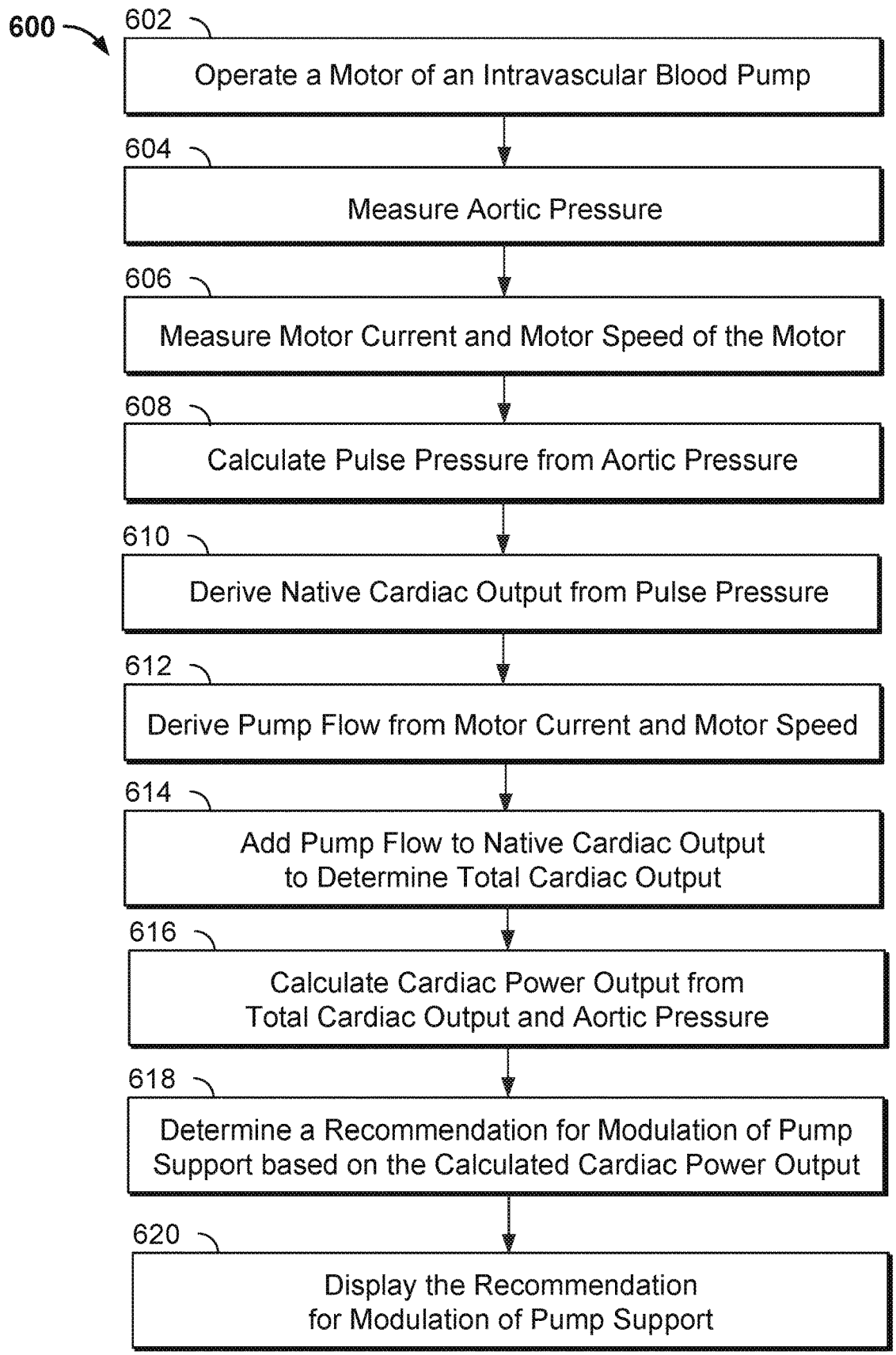
FIG. 6 shows a process for determining a cardiac power output and displaying a recommendation for modulation of pump support to a user.

FIG. 6 shows a process 600 for determining a cardiac power output and displaying a recommendation of modulation of pump support to a user. The process 600 can be performed using the intravascular heart pump system 100 of FIG. 1, or any other suitable heart pump. The cardiac power output, and historical trends in the cardiac power output over time, can be interpreted and evaluated by a physician in an intensive care setting or catheterization lab to monitor metric trends during the weaning process and to assess patient readiness to wean the heart from the blood pump support. Additionally, cardiac output, native cardiac output, and LVEDP can also be generated and displayed to the physician to inform decisions about weaning of a patient.

In order to determine the cardiac power output of a patient, the algorithm proceeds according to the following process. In step 602, the motor of a heart pump is operated. The motor may be operated at a constant rotational speed. In step 604, the aortic pressure is measured. The aortic pressure may be measured by a pressure sensor coupled to the heart pump, by a separate catheter, by a noninvasive pressure sensor, or by any other suitable sensor. The pressure sensor may be a fluid-filled tube, a differential pressure sensor, hydraulic sensor, piezo-resistive strain gauge, optical interferometry sensor or other optical sensor, MEMS piezoelectric sensor, or any other suitable sensor. In some implementations, ventricular pressure is measured in addition to or in alternative to measuring aortic pressure.

In step 606, the current delivered to the motor is measured and the motor speed is measured. The current may be measured using a current sensor or by any other suitable means.

In step 608, the pulse pressure wave is calculated from the aortic pressure waveform by subtracting the minimum aortic pressure from the maximum aortic pressure. The mean aortic pressure may also be extracted from the average of the aortic pressure waveform. In step 610 the native cardiac output is derived from the pulse pressure. To calculate the native cardiac output, a relationship between the pulse pressure and the native cardiac output by a linear scaling factor must first be determined. The scaling factor is specific to both the patient and the condition, and may be derived from internal or external calibration methods. In step 612, the pump flow is derived from the measured motor current and motor speed. In step 614, the total cardiac output is determined by adding the pump flow to the native cardiac output. In step 616, the cardiac power output is calculated from the total cardiac output and the mean aortic pressure.

In step 618, a recommendation for modulation of the pump support to the heart is determined based on the calculated cardiac power output. For example, a recommendation to decrease pump support to wean the patient from cardiac support may be determined if the calculated cardiac power output, or comparison of the calculated cardiac power output to a threshold or historical value, indicates that the patient has improved cardiac function. In another example, a recommendation to increase pump support to the patient may be determined if the calculated cardiac power output, or comparison of the calculated cardiac power output to a threshold or historical value, indicates that the cardiac function has worsened. Finally, in step 620, the recommendation for modulation of pump support is generated for display and displayed on a user interface. In some implementations, the cardiac power output, and additionally other calculated metrics and parameters, are also generated for display and displayed with the recommendation for modulation of pump support. The calculated cardiac power output, and optionally the historical view of the cardiac power output over time, allows the clinician to view and make decisions based on the trends of the cardiac power output, for example to make decisions related to the weaning of a patient from blood pump support. Displaying these metric trends can help a clinician to evaluate the displayed recommendation of modulate and to support weaning decisions or other decisions to change the level of support provided by the blood pump.

The cardiac power output is a product of the cardiac output and the mean aortic pressure, and is indicative of the true measure of power coming from the heart and the pump immediately distal to the aortic valve. This is measureable based on the positioning of the pressure sensor at the pump outflow of the blood pump and the understanding of the operation of the blood pump with respect to the cardiac parameters. Clinicians can use the native cardiac power output as a measure of the overall health of the heart, as it represents the power being output by the heart itself. The trends of the native cardiac power output can be used by a clinician to determine if the native heart output is improving or declining and can make clinical decisions about the support being provided by the blood pump and pharmaceutical therapies based on these trends. The determination of cardiac power output by the algorithm described above is more reliable and accurate than such conventional methods of determination.

Figure 7:
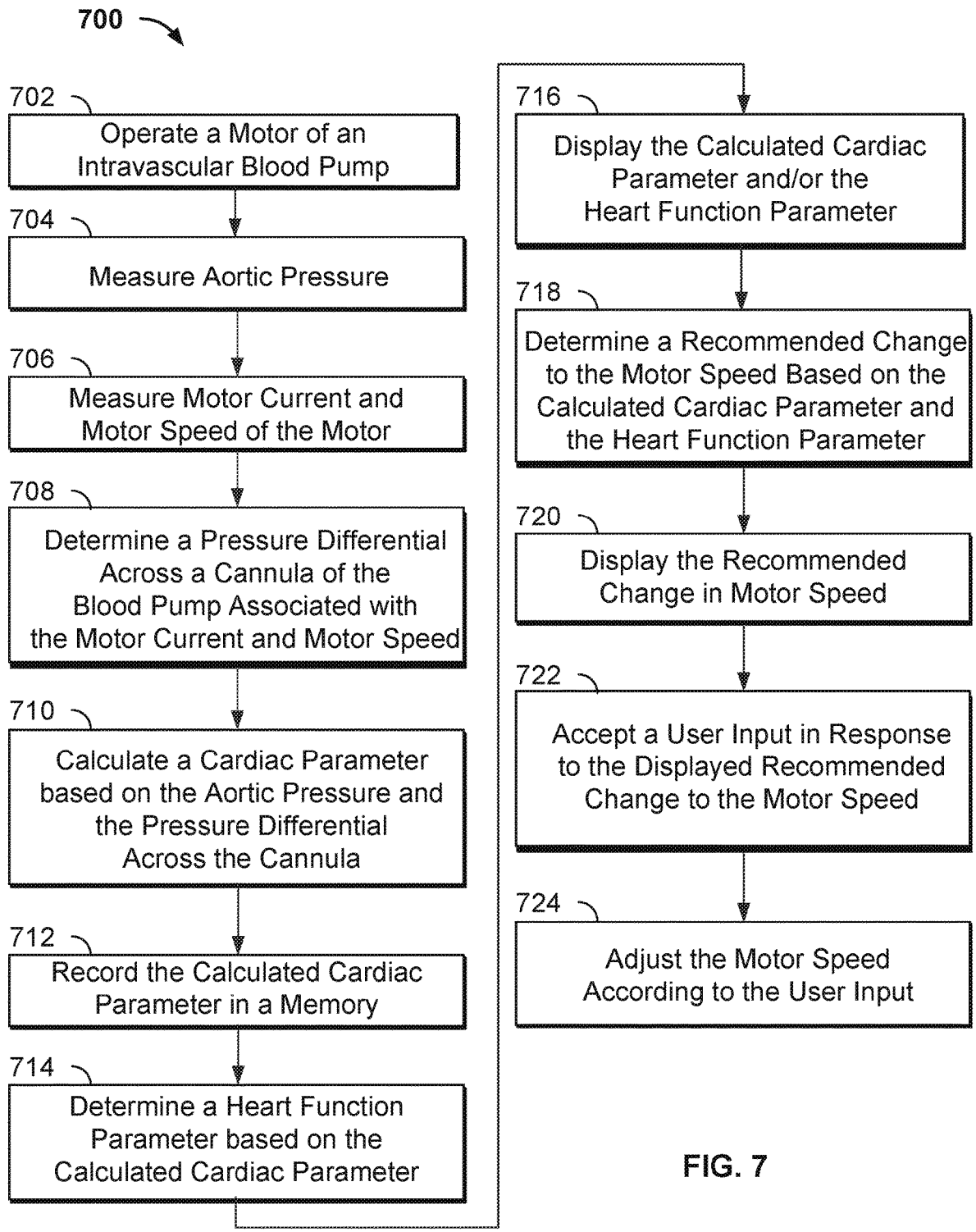
FIG. 7 shows a process for recommending an adjustment to a motor speed based on measured and calculated cardiac parameters.

FIG. 7 shows a process 700 for recommending an adjustment to a motor speed based on measured and calculated cardiac parameters. The process 700 can be performed using the intravascular heart pump system 100 of FIG. 1, or any other suitable heart pump. The process 700 includes steps 702-716 which are substantially similar to steps 402-416 in FIG. 4. These steps are recited briefly here, but a person of ordinary skill will understand that the alternatives and additional details included in the description of the corresponding steps in FIG. 4 also apply to steps 702-716 of FIG. 7.

As in process 400 in FIG. 4, in step 702, the motor of a heart pump is operated. The motor may be operated at a constant rotational speed. In step 704, the aortic pressure is measured. As in process 400 in FIG. 4, the aortic pressure may be measured by a pressure sensor coupled to the heart pump or by a separate catheter. The sensor may be a fluid-filled tube, a differential pressure sensor, hydraulic sensor, piezo-resistive strain gauge, optical interferometry sensor or other optical sensor, MEMS piezo-electric sensor, or any other suitable sensor. In step 706, the current delivered to the motor is measured and the motor speed is measured. In step 708, the pressure differential across a cannula of the blood pump is determined based on the measured motor current and motor speed, by using a lookup table or accessing a function which accounts for the measured motor current for a known motor speed, and optionally other parameters as discussed in regard to process 400 in FIG. 4.

In step 710, a cardiac parameter is calculated based on the pressure differential across the cannula of the blood pump and the aortic pressure. The cardiac parameter may be one of a LVEDP, LVP, aortic pulse pressure, mean aortic pressure, pump flow, pressure gradient, or heart rate. These cardiac parameters can each be used by clinicians as a measure of various aspects of cardiac health and function. The trends of each of the cardiac parameters over time can be used by a clinician to determine if the native heart output is improving or declining and can make clinical decisions about the support being provided by the blood pump and pharmaceutical therapies based on these trends. In some implementations, more than one cardiac parameter is calculated based on the pressure differential across the cannula of the blood pump and the aortic pressure.

In step 712, the calculated cardiac parameter is recorded in the memory. By accessing the recorded cardiac parameters stored in the memory, a historical view of the cardiac parameter over time can be accessed by a user or displayed on a display console as a trend line.

In step 714, a heart function parameter is determined based on the calculated cardiac parameter. The heart function parameter can be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. These heart function parameters can be calculated from the calculated cardiac parameter and other available measured parameters. The heart function parameters offer additional information to clinicians about the heart function. In some implementations, the heart function parameter is also recorded in the memory in order to provide historical data and heart function parameter trends with respect to time. In some implementations, more than one heart function parameter is determined.

In step 716, the calculated cardiac parameter and/or the heart function parameter is generated for display and is displayed to a user. The calculated cardiac parameter and/or heart function parameter is accessed from the memory and is generated for display as a number value, maximum and minimum value over a period of time, and/or as a historical trend over time. The cardiac parameter and heart function parameter is then displayed to a clinician on a display, such as display 300 in FIG. 3. The calculated cardiac parameter, the heart function parameter, and optionally the historical views of the cardiac parameter and/or heart function parameter over time, allows a clinician to view and make decisions based on the trends of the cardiac parameter and heart function parameter.

The display and/or the determination of the cardiac parameter and heart function parameter can be continuous or nearly continuous while the heart pump is implanted in the heart. This can be advantageous over conventional catheter-based methods that only allow sampling of cardiac function at specific times during the cardiac cycle or at discrete points in time. For example, continuous monitoring of the cardiac parameter may allow more rapid detection of cardiac deterioration. Continuous monitoring of the cardiac parameter and heart function parameter can illustrate changes in the heart condition over time. Additionally, if the cardiac assist device is already in the patient, the cardiac function can be measured without having to introduce an additional catheter into a patient. The cardiac parameter and/or heart function parameter may be displayed as shown in the user interface of FIG. 3 or using any other suitable user interface or report.

In step 718, a recommended change to the motor speed is determined based on the calculated cardiac parameter and heart function parameter. The recommended change to the motor speed may be determined based on a comparison of the cardiac parameter and/or the heart function parameter to a threshold value. Subsequently, the cardiac parameter and/or the heart function parameter, or a difference between the cardiac parameter or heart function parameter and the threshold value may be used to determine a required increase or decrease in pump flow, and the increase or decrease in pump flow may be used to determine a corresponding motor speed using a look-up table or other function.

In step 720, the recommended change to the motor speed is generated for display and is displayed. The recommended change to the motor speed can be displayed in the user interface of FIG. 3. In some implementations, the recommended change to the motor speed is displayed on the main screen. In some implementations, the recommended change to the motor speed is displayed as a pop-up or warning. In step 722, a user input is accepted in response to the displayed recommended change to the motor speed. In step 724, the motor speed is adjusted according to the user input. The motor speed is adjusted by changing the power delivered to the motor. The motor speed may be adjusted to be faster or slower than a current speed of the motor depending on the user input in response to the recommended change in motor speed. The power delivered to the motor can be adjusted automatically by a controller or manually (e.g., by a healthcare professional). The degree of support can be increased when a patient's heart function is deteriorating or the degree of support can be decreased when a patient's heart function is recovering, thus allowing the patient to be gradually weaned off of the therapy. This can allow the device to dynamically respond to changes in heart function to promote heart recovery. It can also be used to intermittently modulate pump support and to diagnose how the heart reacts, e.g., if it can take over the pumping function from the heart pumping device.

Figure 8:
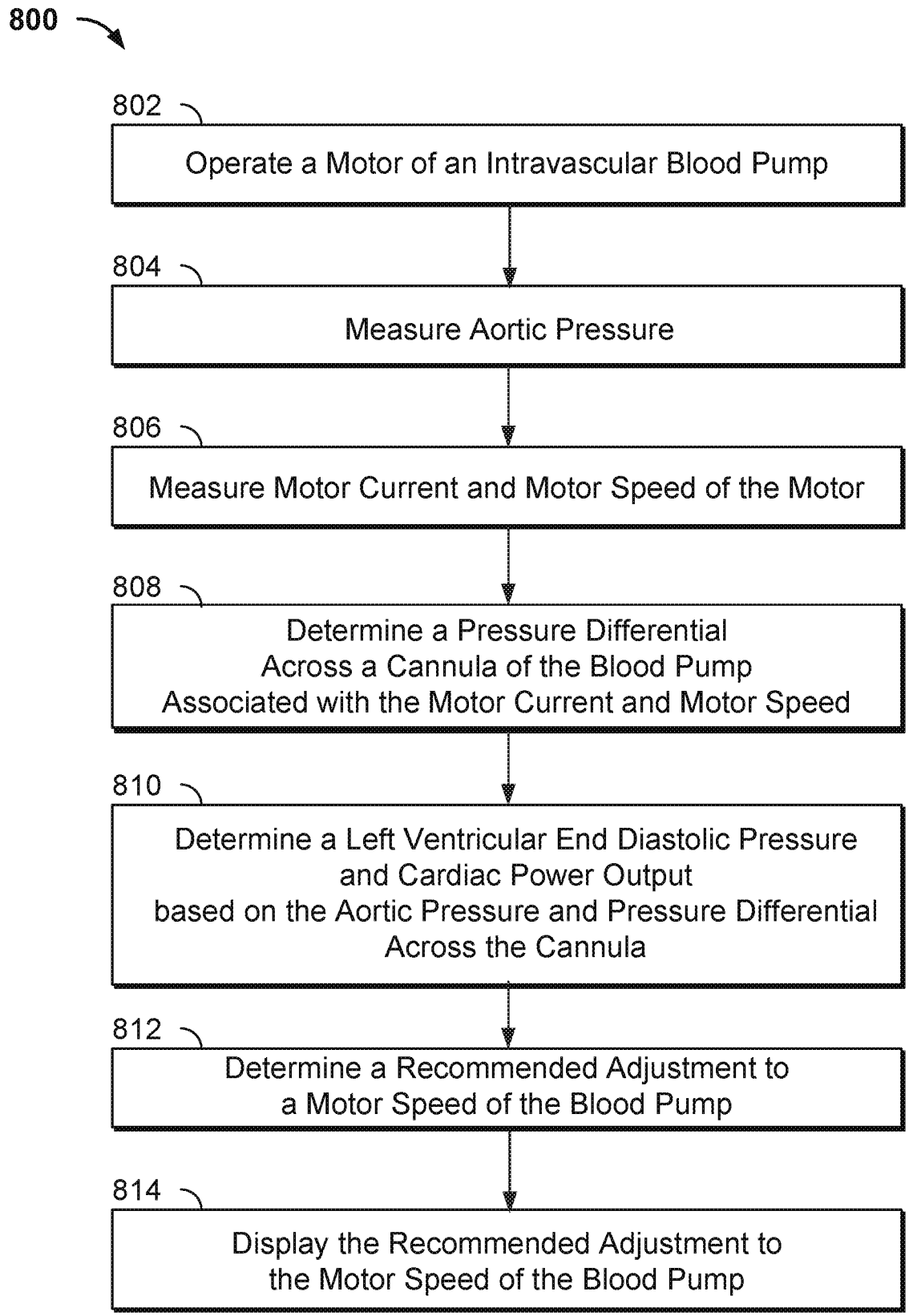
FIG. 8 shows a process for recommending an adjustment to a motor speed based on a cardiac power output and LVEDP.

FIG. 8 shows a process 800 for recommending an adjustment to a motor speed based on a cardiac power output and LVEDP. The process 800 can be performed using the intravascular heart pump system 100 of FIG. 1, or any other suitable heart pump. The process 800 follows the steps of process 700 shown in FIG. 7 for the particular case of determining a recommendation of an adjustment to the motor speed based on the cardiac power output and LVEDP. In step 802, the motor of a heart pump is operated. The motor may be operated at a constant rotational speed. In step 804, the aortic pressure is measured. The aortic pressure may be measured by a pressure sensor coupled to the heart pump, by a separate catheter, by a noninvasive pressure sensor, or by any other suitable sensor. The pressure sensor may be a fluid-filled tube, a differential pressure sensor, hydraulic sensor, piezo-resistive strain gauge, optical interferometry sensor or other optical sensor, MEMS piezo-electric sensor, or any other suitable sensor. In some implementations, ventricular pressure is measured in addition to or in alternative to measuring aortic pressure. In step 806, the current delivered to the motor is measured and the motor speed is measured. The current may be measured using a current sensor or by any other suitable means.

In step 808, the pressure differential across a cannula of the blood pump is determined based on the measured motor current and motor speed. The controller may access a look-up table, such as a look-up table based on the relationship between the differential pressure and the motor current for a known motor speed in FIG. 2A. The controller may alternatively utilize a function describing the relationship between the differential pressure and the motor current to determine the differential pressure across the cannula of the blood pump associated with the measured motor current and a known motor speed. The controller may also take into account various other parameters in the determination of the differential pressure, for example characteristics of the blood pump, pump controller or console, environmental parameters, and motor speed settings, in order to more accurately determine the pressure gradient across the cannula.

In step 810, a LVEDP and a cardiac power output are determined based on the aortic pressure and the pressure gradient across the blood pump cannula. The LVEDP is calculated by subtracting the pressure gradient across the cannula determined from the motor current from the aortic pressure and selecting the end-diastolic point from the cardiac cycle. The cardiac power output is calculated by first determining a native cardiac output from a pulse pressure, determining a total cardiac output based on the pump flow, and finally using the cardiac output with the mean arterial pressure to calculate the cardiac power output. In some implementations, if the blood pump is a right heart blood pump the right ventricular pressure is determined.

In step 812, a recommended adjustment to the motor speed of the blood pump is determined. The recommended adjustment to the motor speed may be determined based on a comparison of the LVEDP, the cardiac power output, the cardiac output, and/or the mean aortic pressure to a threshold value. Subsequently, the above compared cardiac parameter, or a difference between the compared cardiac parameter or heart function parameter and the threshold value may be used to determine a required increase or decrease in pump flow, and the increase or decrease in pump flow may be used to determine a corresponding motor speed using a look-up table or other function.

In step 814, the recommended adjustment to the motor speed of the blood pump is generated for display and is displayed. The recommended change to the motor speed can be displayed in the user interface of FIG. 3. In some implementations, the recommended change to the motor speed is displayed on the main screen. In some implementations, the recommended change to the motor speed is displayed as a pop-up notification or warning.

Figure 9:
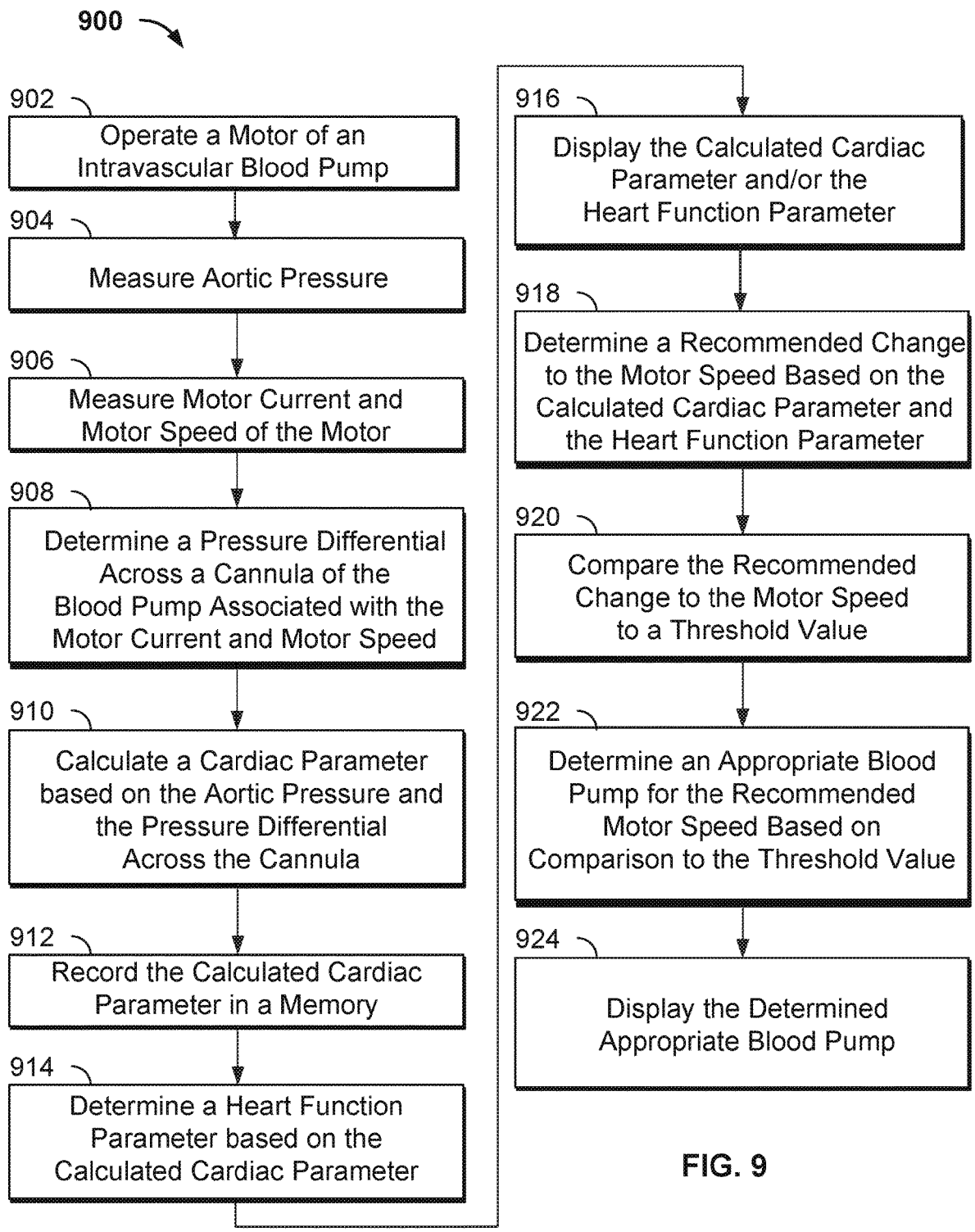
FIG. 9 shows a process for recommending a higher flow device for treatment based on measured and calculated cardiac parameters.

FIG. 9 shows a process 900 for recommending a higher flow device for treatment based on measured and calculated cardiac parameters. The process 900 includes steps 902-918 which are substantially similar to steps 702-718 in FIG. 7. These steps are recited briefly here, but a person of ordinary skill will understand that the alternatives and additional details included in the description of the corresponding steps in FIG. 7 also apply to steps 902-918 of FIG. 9.

In step 902, the motor of a heart pump is operated. In step 904, the aortic pressure is measured. In step 906, the current delivered to the motor is measured and the motor speed is measured. In step 908, the pressure differential across a cannula of the blood pump is determined based on the measured motor current and the measured motor speed. In step 910, a cardiac parameter is calculated based on the pressure differential across the cannula of the blood pump and the aortic pressure. In step 912, the calculated cardiac parameter is recorded in the memory. The calculated cardiac parameter may be any of LVEDP, LVP, aortic pulse pressure, mean aortic pressure, pump flow, pressure gradient, or heart rate. In step 914, a heart function parameter is determined based on the calculated cardiac parameter. The heart function parameter may be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. In step 916, the calculated cardiac parameter and/or the heart function parameter is generated for display and is displayed to a user. The recorded cardiac parameter is accessed in the memory and is processed for display as an instantaneous value, a set of maximum and minimum values over a period of time, and/or as a historical trend over time. The recorded cardiac parameter is then displayed to a user. In some implementations, the calculated heart function parameter is also stored and displayed as a trend over time. In step 918, a recommended change to the motor speed is determined based on the calculated cardiac parameter and heart function parameter.

In step 920, the recommended change to the motor speed is compared to a threshold value. The threshold value may be a value associated with the blood pump, indicating a maximum or minimum operational motor speed. The recommended change to the motor speed is compared to a threshold value in order to determine if the current blood pump is capable of operating at the required speed and/or whether the current blood pump is the optimal blood pump for operation at the required speed.

In step 922, an appropriate blood pump for operation at the recommended motor speed is determined based on the comparison to the threshold value. The appropriate blood pump may be determined by consulting a look-up table including properties and characteristics of various available blood pumps. The determination of the appropriate blood pump for operation at the recommended motor speed may also take into account the calculated cardiac parameter and/or the heart function parameter. Accounting for the calculated cardiac parameter and/or the heart function parameter may enable the controller to make a recommendation based not only on the recommended pump speed, but also on the general heart function and health. In some cases, it may be unwise to change to a different blood pump because of the poor cardiac function of a patient. Taking the calculated cardiac parameter and heart function into account, or alternatively, displaying a warning to the clinician with the recommendation, prevents changing the blood pump to adjust a motor speed when it would be unwise to do so.

In step 924, the determined appropriate blood pump is generated for display and is displayed. The cardiac parameter and heart function parameter can be displayed to a clinician on a display, such as display 300 in FIG. 3. In some implementations, the recommended motor speed is also displayed. As noted above, additional information or warnings to the clinician can also be displayed when a different blood pump is recommended, prompting the clinician to follow protocols or to make additional determinations of heart function and health before acting on the recommendation.

Figure 10:
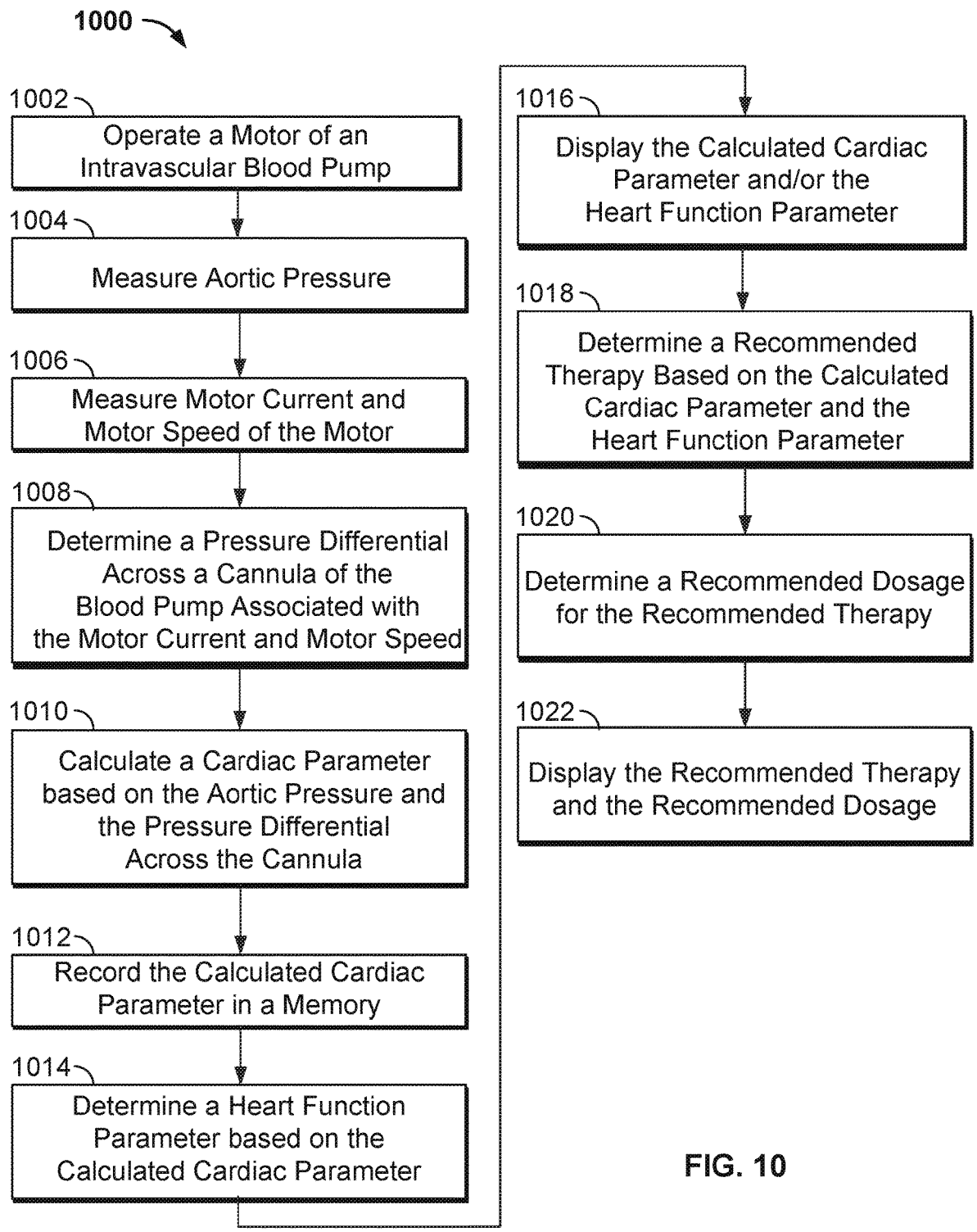
FIG. 10 shows a process for recommending a pharmaceutical therapy based on measured and calculated cardiac parameters.

FIG. 10 shows a process 1000 for recommending a pharmaceutical therapy based on measured and calculated cardiac parameters. For example, the titration of medicaments, including inotropes and vasopressors, can be monitored and determined based on the evaluation of cardiac metrics such as cardiac output, mean aortic pressure and others. Further, volume status and fluid responsiveness can be monitored by evaluation of the LVEDP over time. The process 1000 for recommending a pharmaceutical therapy includes steps 1002-1020 which are substantially similar to steps 702-720 in FIG. 7. These steps are recited briefly here, but a person of ordinary skill will understand that the alternatives and additional details included in the description of the corresponding steps in FIG. 7 also apply to steps 1002-1020 of FIG. 10.

In step 1002, the motor of a heart pump is operated. In step 1004, the aortic pressure is measured. In step 1006, the current delivered to the motor is measured and the motor speed is measured. In step 1008, the pressure differential across a cannula of the blood pump is determined based on the measured motor current and measured motor speed. In step 1010, a cardiac parameter is calculated based on the pressure differential across the cannula of the blood pump and the aortic pressure. The calculated cardiac parameter may be any of LVEDP, LVP, aortic pulse pressure, mean aortic pressure, pump flow, pressure gradient, or heart rate. In step 1012, the calculated cardiac parameter is recorded in the memory. In step 1014, a heart function parameter is determined based on the calculated cardiac parameter. The heart function parameter may be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. In some implementations, the heart function parameter is also stored in the memory. In step 1016, the calculated cardiac parameter and/or the heart function parameter is displayed.

In step 1018, a recommended therapy is determined based on the calculated cardiac parameter and heart function parameter. The recommended therapy is based on the calculated cardiac parameter and heart function parameter. In some implementations, the recommended therapy is based on a comparison of the calculated cardiac parameter and/or the heart function parameter to a threshold value. In some implementations, the recommended therapy is based on a comparison of a change in the calculated cardiac parameter and/or the heart function parameter over a period of time. In some implementations, the recommended therapy is determined by accessing a look-up table and extracting a dosage corresponding to a current value of the calculated cardiac parameter and heart function parameter.

For example, a combination of the calculated cardiac parameters of native cardiac output, LVEDP, and cardiac power output can be analyzed by the algorithm and compared to threshold values to determine that a pharmaceutical intervention is warranted or would be beneficial. The algorithm may determine that the administration of inotropes is warranted, and further analysis such as consultation of a look-up table of dosages may allow the algorithm to provide the recommendation that the clinician administer inotropes as well as a recommendation for the particular dosage or titration with which the therapy should be administered.

Monitoring and analyzing additional cardiac parameters allows the algorithm to also provide information and recommendations to clinicians to modulate the fluid intake of a patient or the administration of diuretics to the patient. By measuring and determining cardiac parameters such as native output, LVEDP, and variation within aortic pulse pressure, the algorithm can identify the status of patients and whether they are in an optimum fluid window) and can also assess and report on the fluid responsiveness of a patient.

In step 1020, a recommended dosage associated with the recommended therapy is determined. The recommended dosage is based on the calculated cardiac parameter and heart function parameter. In some implementations, the recommended dosage is based on a comparison of the calculated cardiac parameter and/or the heart function parameter to a threshold value. In some implementations, the recommended dosage is based on a comparison of a change in the calculated cardiac parameter and/or the heart function parameter over a period of time. In some implementations, the recommended dosage is determined by accessing a look-up table for the recommended therapy and extracting a dosage corresponding to a current value of the calculated cardiac parameter and heart function parameter.

In step 1022, the recommended therapy and the recommended dosage are generated for display and are displayed. The recommended therapy and the recommended dosage can be displayed in the user interface of FIG. 3. In some implementations, the recommended therapy and the recommended dosage is displayed on the main screen. In some implementations, the recommended therapy and the recommended dosage is displayed as a pop-up or warning. In a similar fashion as in the process 900, the recommended therapy and recommended dosage may be displayed with a warning to a clinician to prompt the clinician to follow specific protocols or to monitor or check other cardiac function parameters before administering any therapy.

Figure 11:
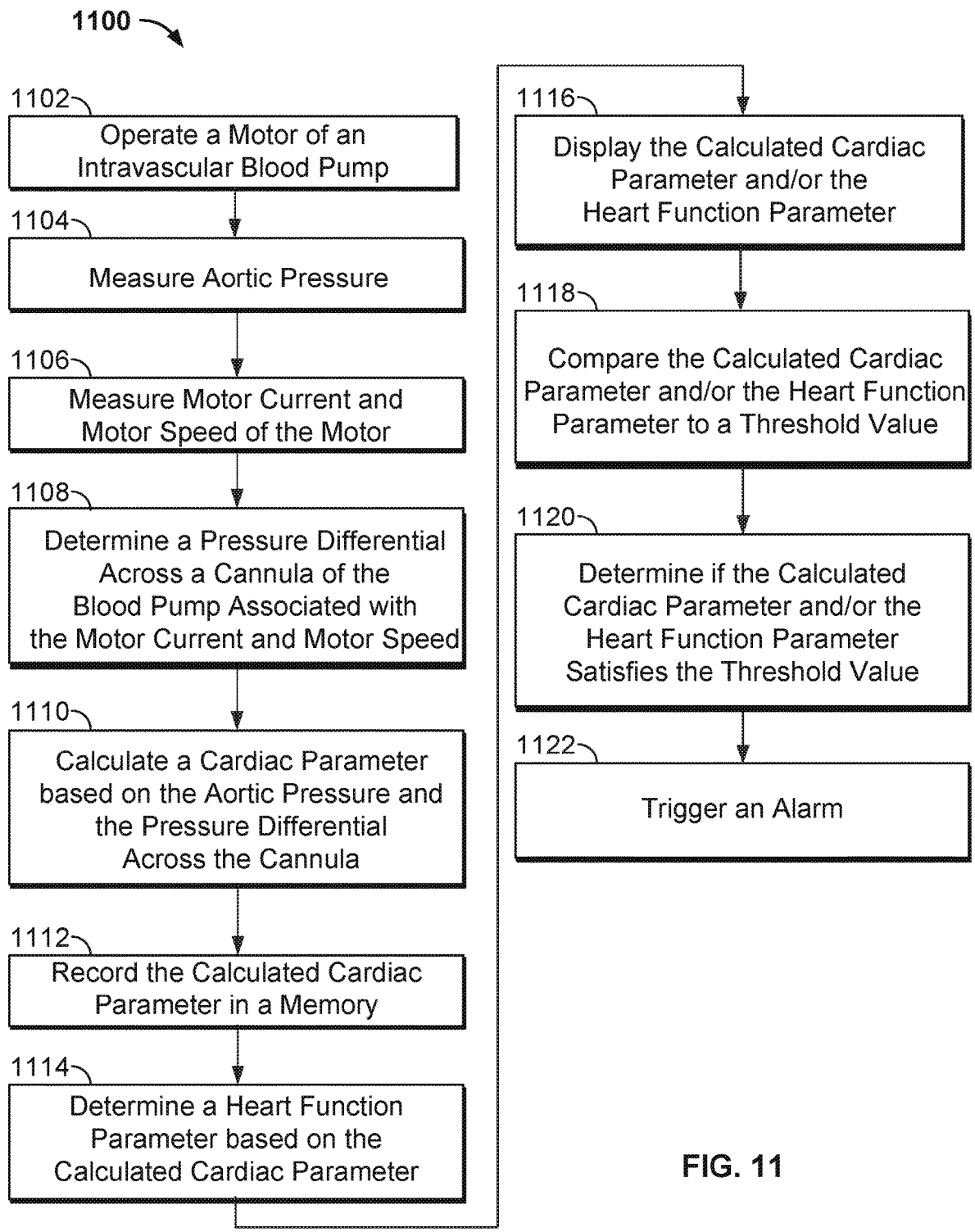
FIG. 11 shows a process for alerting a user of predicted adverse cardiac events based on measured and calculated cardiac parameters; a FIG. 12 shows a process for balancing right and left-sided blood pump devices during bi-ventricular support based on measured and calculated cardiac parameters.

FIG. 11 shows a process 1100 for alerting a user of predicted adverse cardiac events based on measured and calculated cardiac parameters. The process 1100 includes steps 1102-1120 which are substantially similar to steps 702-720 in FIG. 7. These steps are recited briefly here, but a person of ordinary skill will understand that the alternatives and additional details included in the description of the corresponding steps in FIG. 7 also apply to steps 1102-1120 of FIG. 11.

In step 1102, the motor of a heart pump is operated. In step 1104, the aortic pressure is measured. In step 1106, the current delivered to the motor is measured and the motor speed is measured. In step 1108, the pressure differential across a cannula of the blood pump is determined based on the measured motor current and measured motor speed. In step 1110, a cardiac parameter is calculated based on the pressure differential across the cannula of the blood pump and the aortic pressure. The calculated cardiac parameter may be any of LVEDP, LVP, aortic pulse pressure, mean aortic pressure, pump flow, pressure gradient, or heart rate. In step 1112, the calculated cardiac parameter is recorded in the memory. In step 1114, a heart function parameter is determined based on the calculated cardiac parameter. The heart function parameter may be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance. In some implementations, the heart function parameter is also stored in the memory. In step 1116, the calculated cardiac parameter and/or the heart function parameter is generated for display and is displayed to a user. The calculated cardiac parameter and/or the heart function parameter can be generated for display as an instantaneous value, a maximum and minimum value over a period of time, and/or as a historical trend over time. The calculated cardiac parameter and/or the heart function parameter is then displayed to the user.

In step 1118, the calculated cardiac parameter and/or the heart function parameter are compared to a threshold value. In some implementations, the set threshold value is a system value set within the controller. In some implementations, the set threshold value is set by a clinician based on a patient's history and health. In some implementations, the set threshold value is a previous value of the cardiac metric, for example, a previous value measured or calculated a predetermined amount of time before. In step 1120, it is determined whether the calculated cardiac parameter and/or the heart function parameter satisfy the threshold value. The set threshold value is set such that a cardiac parameter or heart function parameter which satisfies the threshold is an indication or possible indication of an early warning signal of a cardiac or ischemic event in progress.

Many adverse events can be predicted based on the determination of cardiac parameters and comparison of the cardiac parameters or their trends over time to a threshold value. Additionally, the display of these additional cardiac parameters to healthcare professionals in real time and including historical data enables physicians to better understand patient health and to predict and address possible adverse events. For example, additional ischemic events, conduction abnormalities, or bleeding and hemolysis can be detected and addressed based on the cardiac parameters calculated and displayed according to the algorithm described herein. Based on the prediction of such adverse events, a physician can make clinical decisions such as optimization of support to maximize native recovery, and balancing of left and right-sided support.

In step 1122, an alarm is triggered with regard to the cardiac parameter and/or the heart function parameter. The alarm can be an audible alarm or can be displayed in the user interface of FIG. 3. In some implementations, the alarm can be sent, via a Wi-Fi network, blue tooth signal, or cellular signal, to a clinician by page, text, or email. In some implementations, the warning is displayed on the main screen. In some implementations, the warning is displayed as a pop-up message. In some implementations, the warning can be turned off or muted by a clinician.

Figure 12:
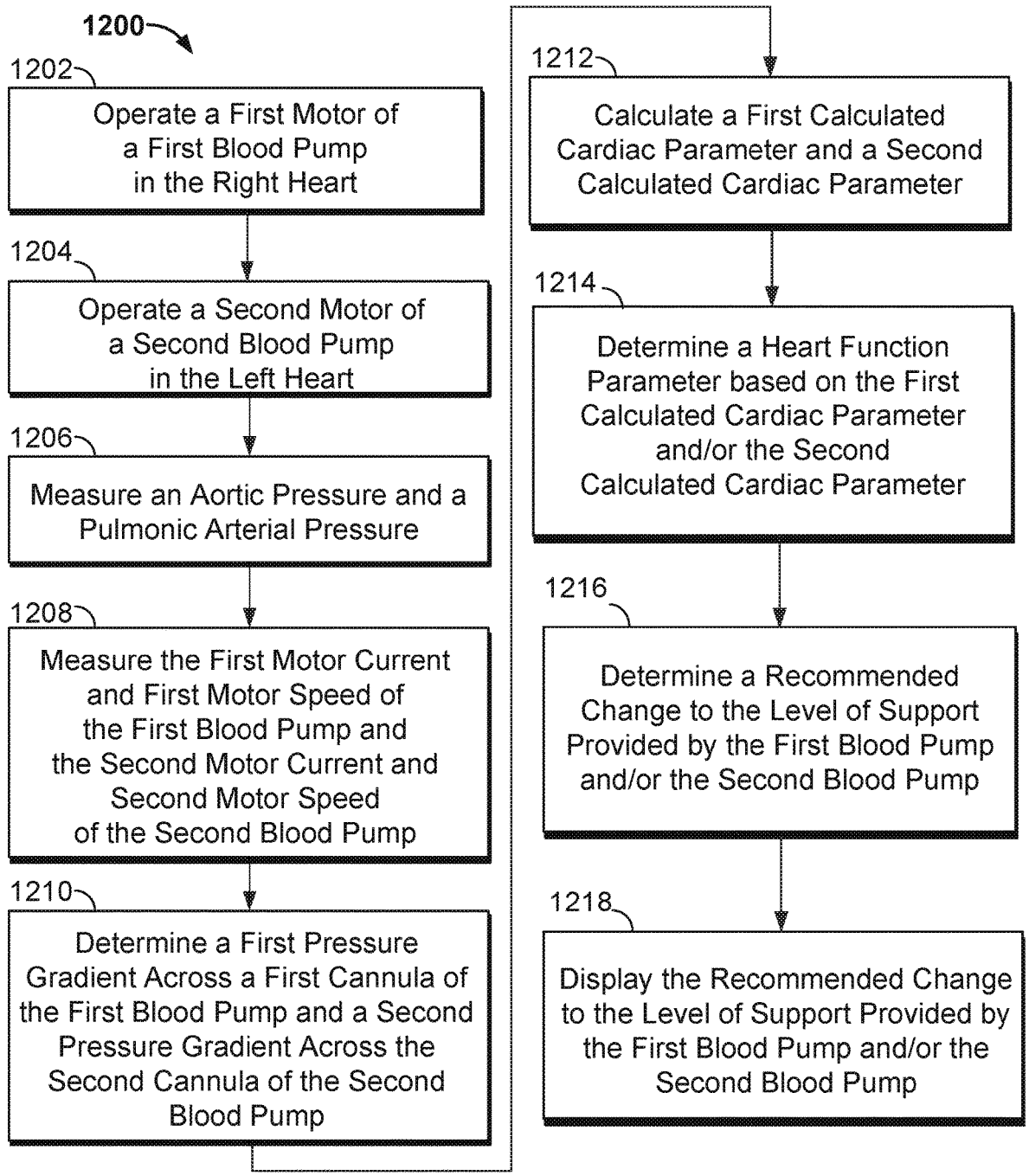

FIG. 12 shows a process 1200 for balancing right and left-sided blood pump devices during bi-ventricular support based on measured and calculated cardiac parameters. When both left-sided and right-sided devices provide simultaneous cardiac support, it can be challenging to balance the right-sided and left-sided output to maintain appropriate pressures in the lungs and limit the risk of pulmonary edema. Measuring native cardiac outputs and total outputs along with the pulmonary artery pressure and left-ventricular diastolic pressure enable clinicians to better balance the right and left side support.

In step 1202, the first motor of a first blood pump is operated. This may be, for example a right-sided device placed in the right ventricle and pulmonary artery of the heart. In step 1204, the second motor of the second blood pump is operated. This may be, for example, a left-sided device placed in the left ventricle and aorta of the heart. The first motor and the second motor are simultaneously operated to provide support to both sides of the heart. At step 1206, the pressure at the pump outlet is measured. For the second pump, a left-side device, this is the aortic pressure. For the first pump, a right-sided device, this is the pulmonic pressure. The aortic pressure may be measured by a pressure sensor coupled to the heart pump, by a separate catheter, by a noninvasive pressure sensor, or by any other suitable sensor. The pressure sensor may be a fluid-filled tube, a differential pressure sensor, hydraulic sensor, piezo-resistive strain gauge, optical interferometry sensor or other optical sensor, MEMS piezo-electric sensor, or any other suitable sensor. In some implementations, ventricular pressure is measured in addition to or in alternative to measuring aortic pressure.

At step 1208, the first motor current and first motor speed of the first blood pump are measured and the second motor current and second motor speed of the second blood pump are measured. In step 1210, the first pressure differential across a first cannula of the first blood pump is determined based on the measured first motor current and measured first motor speed, and the second pressure differential across a second cannula of the second blood pump is determined based on the measured second motor current and measured second motor speed. The first pressure differential and the second pressure differential may be determined by using a lookup table or accessing a function which accounts for the measured motor current, measured motor speed, and optionally other parameters.

In step 1212, a first cardiac parameter is calculated based on the first pressure differential across the first cannula of the first blood pump and the first pump outlet pressure, and a second cardiac parameter is calculated based on the second pressure differential across the second cannula of the second blood pump and the second pump outlet pressure. The first cardiac parameter, from the right-sided device may be any of a right ventricular pressure, a right ventricular end-diastolic pressure, a pulmonary artery pressure, a right arterial pressure, a central venous pressure, or a blood pump flow rate. The second cardiac parameter, from the left-sided device, may be any of a LVEDP, LVP, aortic pulse pressure, mean aortic pressure, pump flow, pressure gradient, heart rate, or right arterial pressure. These cardiac parameters can each be used by clinicians as a measure of various aspects of cardiac health and function and to better balance the right and left-sided devices to provide balanced cardiac support.

Further, the trends of each of the cardiac parameters over time can be used by a clinician to determine if the native heart output is improving or declining and can make clinical decisions about the support being provided by the blood pumps and pharmaceutical therapies based on these trends. In some implementations, more than one cardiac parameter is calculated based on the pressure differential across the cannula of the blood pump and the aortic pressure.

In step 1214, a heart function parameter is determined based on the calculated first cardiac parameter and/or the calculated second cardiac parameter. The heart function parameter can be any of cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance, or similar parameters associated with right-side support. These heart function parameters can be calculated from the calculated cardiac parameters and other available measured parameters. The heart function parameters offer additional information to clinicians about the heart function and about the balance of the support being provided by the first blood pump and the second blood pump. In some implementations, the heart function parameter is also recorded in the memory in order to provide historical data and heart function parameter trends with respect to time. In some implementations, more than one heart function parameter is determined.

In step 1216, a recommended change to the level of support provided by the first blood pump and/or the second blood pump is determined. The recommended change to the level of support may be accessed in a look-up table stored in the memory, or may be calculated based on current or historical values of the cardiac parameters and heart function parameters. The recommended change to the level of support may include a prompt to increase or decrease pump support, and/or may include a recommendation of an amount of change to be made to the pump support.

In step 1218, the recommended change to the level of support provided by the first blood pump and/or the second blood pump is generated for display and is displayed. The recommended change to the level of support provided by the first blood pump and/or the second blood pump can be displayed in the user interface of FIG. 3. In some implementations, the recommended change to the level of support provided by the first blood pump and/or the second blood pump is displayed on the main screen. In some implementations, the recommended change to the level of support provided by the first blood pump and/or the second blood pump is displayed as a pop-up or warning. The recommended change to the level of support provided by the first blood pump and/or the second blood pump may be displayed to a clinician with additional information about the first and second blood pumps, and with prompts to follow protocols and conduct further checks before changing the level of support provided by adjustment of the motor speed of the first blood pump or the second blood pump. In some implementations, the controller may determine the appropriate change in motor speed to one or both of the first blood pump and the second blood pump, and may also determine if the first blood pump and the second blood pump currently providing support are the optimal blood pumps to operate at a recommended motor speed to provide the recommended level of support.

Using the data collected by the one or more blood pumps and blood pump systems to calculate clinically relevant cardiac parameters and heart function parameters and displaying the parameters to clinicians in real-time provides clinicians with important information about cardiac health and function that can be used to make clinical decisions about support. Further, algorithms within the blood pump controller or console which aid clinicians in determining potential issues and provide recommendations to improve cardiac function give clinicians the ability to detect issues earlier and to respond to problems more quickly than they can without this important information.

Figure 13:
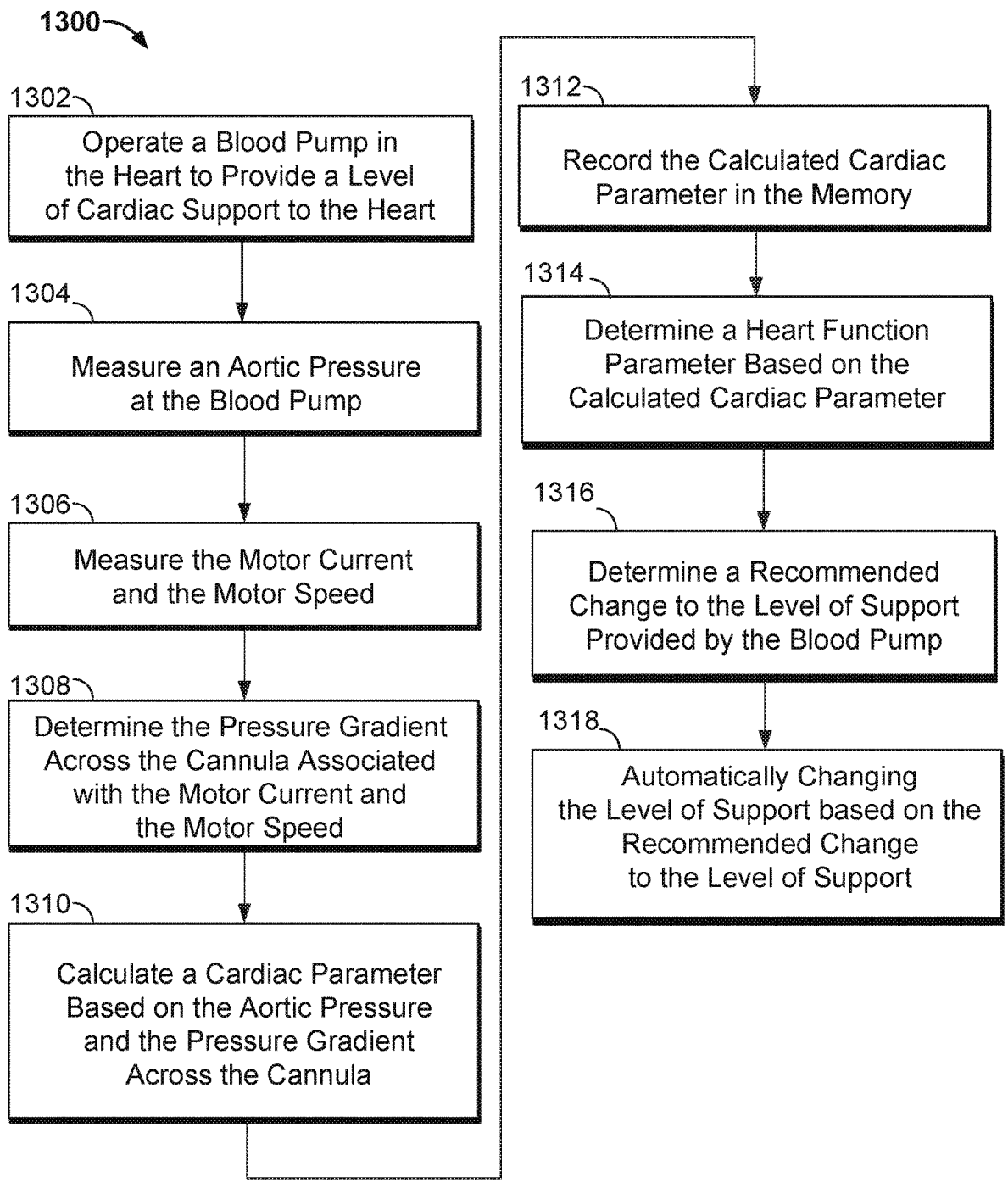
FIG. 13 shows a process for automatically modifying a level of support provided by the blood pump.

FIG. 13 shows a block diagram 1300 of a process for automatically modifying the level of support provided by a blood pump. In step 1302 a blood pump positioned in the heart is operated to provide a level of cardiac support to the heart. The blood pump has a cannula and a motor operating at a motor speed and drawing a variable current to provide the support to the heart. At step 1304, a controller coupled to the blood pump measures the aortic pressure in the heart. At step 1306, the controller measures the motor current and the motor speed. At step 1308, the controller determines a pressure gradient across the cannula associated with the motor current and the motor speed.

At step 1310, a processor calculates a calculated cardiac parameter based on the aortic pressure and the pressure gradient across the cannula associated with the motor current and the motor speed. At step 1312, the calculated cardiac parameter is recorded in a memory. At step 1314, a heart function parameter is determined based on the calculated cardiac parameter. In some implementations, the heart function parameter is also stored in the memory. At step 1316, a recommended change to the level of cardiac support provided by the blood pump is determined based on at least one of the calculated cardiac parameter and the heart function parameters. At step 1318, the recommended change to the level of cardiac support is generated for display.

In some implementations, more than one cardiac parameter is calculated from the aortic pressure and the pressure gradient across the cannula. For example, any number of cardiac parameters can be calculated, including LVEDP, LVP, aortic pulse pressure, mean aortic pressure, pump flow, pressure gradient, or heart rate. In some implementations, these cardiac parameters are also generated for display as maximum or minimum values, average values, instantaneous values, historical trends, or waveforms. In some implementations, more than one heart function parameter is determined from the cardiac parameters. For example, the heart function parameter may be a cardiac output, cardiac power output, native cardiac output, native cardiac power output, cardiac contractility, cardiac relaxation, fluid responsiveness, volume status, cardiac unloading index, cardiac recovery index, left-ventricular diastolic function, left-ventricular diastolic elastance, left-ventricular systolic elastance, stroke volume, heart rate variability, stroke volume variability, pulse pressure variability, aortic compliance, vascular compliance, or vascular resistance.

In some implementations, the calculated cardiac parameter is a LVEDP and the heart function parameter is a cardiac power output. By calculating the LVEDP and cardiac power output, a recommendation for modulation of cardiac support can be determined based on historical data. Based on the patient cardiac health as illustrated by the LCEDP and cardiac power output, a recommendation to increase the motor speed (to provide increased cardiac support by the blood pump for patients with failing health) or to decrease the motor speed (to wean a patient with improving health from the blood pump) may be determined, generated for display, and displayed to a health care professional.

Such recommendations may be determined by comparing a current value of the LVEDP and/or cardiac power output to a previous value or to a set threshold value. Based on the comparison, a look up table stored in the memory may provide a recommendation which can include an indication of the determined recommended change in support level, as well as a list of steps to achieve the recommended change. Alternatively, in some implementations, the recommended change in the level of cardiac support can be automated by the controller.

Various combinations of cardiac metrics and parameters can be useful in determining aspects of patient cardiac health and functioning of both the heart and the blood pump. The values of these parameters, as well as recommendations and warnings generated by the algorithms based on historical information or present thresholds based on patient health, enable health care professionals to make informed decisions about modulation of support, as well as a number of other healthcare decisions as described above in reference to FIGS. 4-12.

Figure 14:
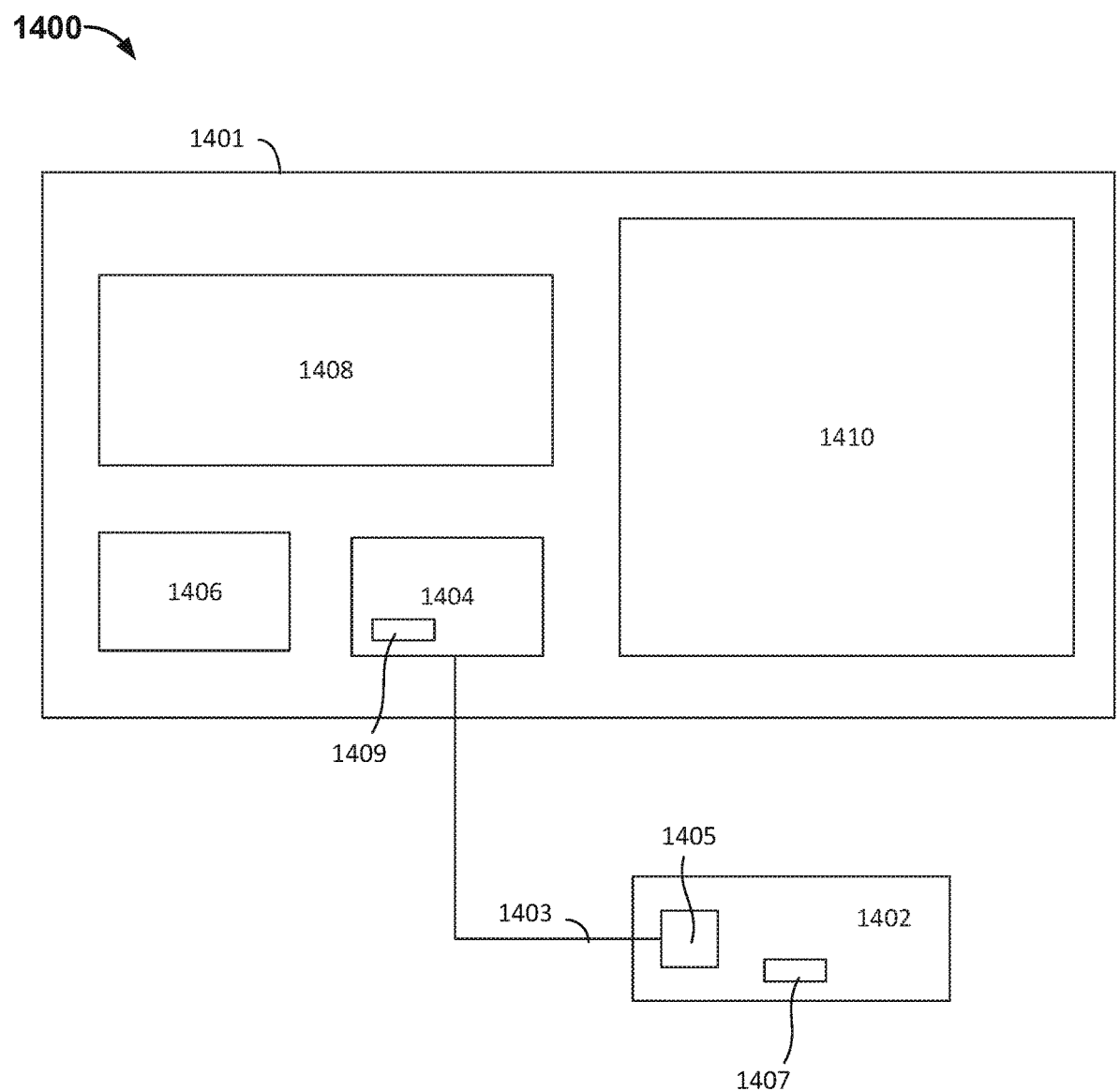
FIG. 14 shows a block diagram of an exemplary blood pump system.

FIG. 14 shows a block diagram of an exemplary blood pump system 1400 to enact any of the methods described above with regard to FIGS. 4-13. The heart pump system 1400 may operate within a heart, partially within the heart, outside the heart, partially outside the heart, partially outside the vascular system, or in any other suitable location in a patient's vascular system. The blood pump system 1400 includes a console 1401 and a blood pump 1402. The console 1401 includes a drive unit 1404, a memory 1406, a processor 1408, circuitry 1403, and a display 1410.

The blood pump system 1400 may be used with any suitable blood pump device, for example, blood pump 1402 may be blood pump 100 shown in FIG. 1, to provide cardiac support to the right or left side of the heart. The blood pump 1402 includes motor 1405 and sensor 1407, as well as other components of blood pump 100 in FIG. 1, which are not shown. In some implementations, the blood pump system 1400 may be used with two blood pumps in order to provide cardiac support to the left and right sides of the heart simultaneously.

The blood pump 1402 is coupled to the drive unit 1404 by circuitry 1403. All or part of the circuitry 1403 may be in the console 1401 separate/remote from the blood pump 1402. In some implementations, the circuitry 1403 is internal to the blood pump 1402. The circuitry 1403 and the blood pump 1402 are not shown to scale. The drive unit 1404 supplies a current to the motor 1405 of the heart pump 1402 by circuitry 1403. The current that the drive unit 1404 supplies to the motor 1405 of the heart pump 1402 over wire 1426 is measured by the current sensor 1409 in or coupled to the drive unit 1404.

The placement signal or aortic pressure is measured at the pressure sensor 1407 located on the blood pump 1402. The pressure detected at the pressure sensor 1307 is received through circuitry 1403 at the drive unit 1404 and may be passed to the processor 1408 along with the current supplied to the motor 1405. In some implementations, the aortic pressure may be measured by a pressure sensor 1407 coupled to the blood pump 1402, by a separate catheter, by a noninvasive pressure sensor, or by any other suitable sensor. The pressure sensor 1407 may be a fluid-filled tube, a differential pressure sensor, hydraulic sensor, piezo-resistive strain gauge, optical interferometry sensor or other optical sensor, MEMS piezo-electric sensor, or any other suitable sensor.

The processor 1408 includes software and/or hardware allowing it to receive the motor current and pressure measurements from the drive unit 1404 and use the values to determine a plurality of additional cardiac parameters and heart function parameters. For example, the processor includes software that uses the methods described with regard to FIGS. 2A-2E to calculate a LVP and LVEDP from the motor current of the blood pump 1402 and aortic pressure information received from the pressure sensor 1407. Further, the processor 1408 is capable of storing received measurements, the parameters and the values in the memory 1406, and of accessing stored values and parameters in the memory for to generate for display on the display 1410.

The processor 1408 further includes algorithms that execute the steps described with regard to FIGS. 4-13 to accept or request values of the current and aortic pressure from the drive unit 1404 and determine from these values cardiac and heart function parameters indicative of a health or function of a heart. The values can also be generated for display to a user and be displayed on the display 1410.

The processor 1408 is capable of accessing functions and look-up tables stored in the memory 1406 in order to make determinations regarding the calculated cardiac and heart function parameters and to use the determinations to make recommendations regarding the treatment and support provided to a patient's heart. The processor 1408 is capable of generating the recommendations and displaying these recommendations on display 1410.

Display 1410 may be substantially similar to the user interface 300 in FIG. 3. The display provides the calculated cardiac parameters and heart function parameters of clinical relevance to clinicians to enable them to make treatment decisions with real-time data. Further, the display 1410 allows the processor 1408 to display recommendations to a clinician to allow clinicians to more quickly detect and respond to life-threatening cardiac issues. The processor 1408 on console 1401 uses the blood pump 1402 and accessible measurements to provide additional information to clinicians to help them to provide more efficient and more effective cardiac therapies to patients.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous insertion of heart pumps, may be applied to apparatuses in other applications.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

We claim:

1. A method for providing cardiac support to a heart, comprising:
operating a blood pump positioned in the heart, the blood pump having a cannula and including a motor operating at a motor speed and drawing a variable motor current to provide a level of cardiac support to the heart;
measuring at a controller coupled to the blood pump, an aortic pressure;
measuring, at the controller, the motor current and the motor speed;
determining a pressure gradient across the cannula associated with the motor current and the motor speed;
using a processor to calculate, from the aortic pressure and the pressure gradient across the cannula associated with the motor current and the motor speed, a calculated cardiac parameter;
recording, in a memory, the calculated cardiac parameter;
determining, based on the calculated cardiac parameter, a heart function parameter;
determining, based on at least one of the calculated cardiac parameter and the heart function parameter, a recommended change to the level of cardiac support provided by the blood pump; and
generating for display the recommended change.

2. The method of claim 1, the method further comprising:
accepting a user input in response to the displayed recommended change to the level of cardiac support provided by the blood pump; and
adjusting the motor speed to adjust the level of cardiac support according to the user input.

3. The method of claim 2, wherein adjusting the motor speed according to the user input comprises increasing the motor speed to increase the flow of blood from the heart.

4. The method of claim 2, wherein adjusting the motor speed according to the user input comprises decreasing the motor speed to wean the heart from the cardiac support.

5. The method of claim 2, wherein the calculated cardiac parameter is at least one of a left-ventricular pressure, a left ventricular end diastolic pressure, an aortic pulse pressure, and a mean aortic pressure.

6. The method of claim 5, wherein the heart function parameter is selected from a cardiac output and a cardiac power output.

7. The method of claim 6, the method further comprising accessing, in the memory, a history of previously recorded cardiac parameters and heart function parameters.

8. The method of claim 7, the method further comprising generating for display at least one of the calculated cardiac parameter and the heart function parameter as a function of time.

9. The method of claim 8, wherein the determined recommended change to the motor speed is based on the history of at least one of the previously recorded cardiac parameters and heart function parameters.

10. The method of claim 9, wherein determining a recommended change in support further comprises:
determining a change in one of the calculated cardiac parameter or the heart function parameter based on the history of previously recorded cardiac parameters and heart function parameters;
determining a recommended alteration in the provided level of cardiac support based on the change; and
converting the recommended alteration in provided level of cardiac support to a recommended change in motor speed.

11. The method of claim 1, the method further comprising:
determining, based on at least one of the calculated cardiac parameter and the heart function parameter, a suction event at an inflow of the blood pump; and
generating for display a warning of a suction event.

12. The method of claim 11, the method further comprising:
identifying, based on at least one of the calculated cardiac parameter and the heart function parameter, a cause of the suction event; and
generating for display a recommendation to address the cause of the suction event.

13. The method of claim 12, wherein identifying the cause of the suction event comprises:
comparing a value of the calculated cardiac parameter to a threshold value, wherein the cardiac parameter is a left ventricular pressure and the threshold is zero; and
comparing a value of the left ventricular pressure over a cardiac cycle to a value of the aortic pressure over a cardiac cycle.

14. The method of claim 13, wherein the method further comprises:
identifying a diastolic suction event if a minimum value of the left ventricular pressure is less than the threshold in a diastole phase but normal in systolic phase of the cardiac cycle.

15. The method of claim 13, wherein the method further comprises:
identifying a systolic suction event if a minimum value of the left ventricular pressure is less than the threshold in the diastolic phase, and a value of the left ventricular pressure does not exceed a value of the aortic pressure over the cardiac cycle.

16. A percutaneous blood pump system comprising:
a blood pump configured to be positioned in a heart, the blood pump comprising:
a cannula;
a sensor configured to measure an aortic pressure in the heart; and
a motor operable at a motor speed and configured to draw a variable motor current to provide a level of cardiac support to the heart; and
a controller configured to control the motor current and motor speed, the controller comprising:
a memory;
a user interface; and
a processor configured to:
measure the motor current and the motor speed of the motor;
receive an indication of the aortic pressure from the sensor and convert the indication of the aortic pressure to an aortic pressure measurement;
determine a pressure gradient across the cannula associated with the motor current and the motor speed;
calculate at least one cardiac parameter based on the aortic pressure measurement and the pressure gradient across the cannula;
record the at least one calculated cardiac parameter in the memory;
calculate, based on the at least one cardiac parameter, one or more heart function parameters;
determine, based on at least one of the at least one cardiac parameter and the one or more heart function parameters, a recommended change to the level of cardiac support to the heart; and
generate for display on the user interface the recommended change to the level of cardiac support.

17. The blood pump system of claim 16, wherein the processor is further configured to calculate a left ventricular pressure as a cardiac parameter and a cardiac power output as a heart function parameter.

18. The blood pump system of claim 17, wherein the processor is further configured to:
record the at least one calculated cardiac parameter in the memory as a first calculated cardiac parameter; and
record a second calculate cardiac parameter in the memory at a later time.

19. The blood pump system of claim 18, the processor further configured to:
access the first cardiac parameter and the second cardiac parameter in the memory; and
determine a recommended change to the motor speed based on a compared value of the first cardiac parameter to the second cardiac parameter.

20. The blood pump system of claim 16, the processor further configured to:

determine, based on at least one of the calculated cardiac parameter and the heart function parameter, a suction event at an inflow of the blood pump; and generate a warning of a suction event for display on the user interface.

\* \* \* \* \*

UNITED STATES PATENT AND TRADEMARK OFFICE
CERTIFICATE OF CORRECTION

PATENT NO. : 10,765,791 B2  
APPLICATION NO. : 16/003669  
DATED : September 8, 2020  
INVENTOR(S) : Christian Moyer et al.

Page 1 of 1

It is certified that error appears in the above-identified patent and that said Letters Patent is hereby corrected as shown below:

In the Specification

Column 17, Line 65 - Delete "528," and insert --532,-- therefor.

Column 17, Line 65 - Delete "532." and insert --528.-- therefor.

Column 19, Line 38 - Delete "504" and insert --503-- therefor.

Column 19, Line 51 - Delete "504." and insert --503.-- therefor.

Column 32, Line 37 - Delete "1307" and insert --1407-- therefor.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*